(12) United States Patent
Mapp et al.

(10) Patent No.: US 7,786,310 B2
(45) Date of Patent: Aug. 31, 2010

(54) SMALL MOLECULE TRANSCRIPTIONAL ACTIVATION DOMAINS

(75) Inventors: Anna K. Mapp, Ann Arbor, MI (US);
Aaron R. Minter, Wilmington, DE (US)

(73) Assignee: The Regents of the University of Michigan, Ann Arbor, MI (US)

( * ) Notice: Subject to any disclaimer, the term of this patent is extended or adjusted under 35 U.S.C. 154(b) by 631 days.

(21) Appl. No.: 11/268,157

(22) Filed: Nov. 7, 2005

(65) Prior Publication Data

US 2007/0105151 A1    May 10, 2007

Related U.S. Application Data

(60) Provisional application No. 60/625,680, filed on Nov. 5, 2004.

(51) Int. Cl.
| | | |
|---|---|---|
| C07D 293/00 | (2006.01) | |
| C07D 421/00 | (2006.01) | |
| C07D 517/00 | (2006.01) | |
| C12Q 1/68 | (2006.01) | |
| C40B 40/04 | (2006.01) | |

(52) U.S. Cl. .............................. 548/100; 435/6; 506/15
(58) Field of Classification Search ................. 548/100; 435/6; 506/15
See application file for complete search history.

(56) References Cited

U.S. PATENT DOCUMENTS

| 5,618,682 A | 4/1997 | Scheirer |
| 5,674,713 A | 10/1997 | McElroy |
| 5,976,796 A | 11/1999 | Szalay |
| 6,074,859 A | 6/2000 | Hirokawai |

OTHER PUBLICATIONS

Minter et al., "A Small Molecule Transcriptional Activation Domain" J. Am. Chem. Soc. Aug. 7, 2004, 126, 10504-10505.*
Fray et al., "The stereoselectivity of Addition of N-Benzyl-C-alkylnitrones to Methyl Crotonate. X-ray Crystal Structure of (3RS,4RS,5RS)-2-Benzyl-4-methoxy-carbonyl-5-methyl-3-[(4RS)-2,2,5,5-tetramethyl-1,3-dioxolan-4-yl]isoxazolidine" J. Chem. Soc. Perkin Trans. I 1985, 2753-2761.*
Ptashne, How eukaryotic transcriptional activators work.; Nature, 1988,335:683.
Roeder, The complexities of eukaryotic transcription initiation: regulation of preinitiation complex assembly.; Trends Biochem. Sci., 1991, 16:402.
Zawel et al., Initiation of transcription by RNA polymerase II: a multi-step process.; Prog. Nucl. Acid Res. Mol. Biol., 1993, 44:67.
Conaway et al., General initiation factors for RNA polymerase II.; Annu. Rev. Biochem. 1993, 62:161.
Buratowski et al., Five intermediate complexes in transcription initiation by RNA polymerase II.; Cell 1989, 56:549.
Choy et al., Eukaryotic activators function during multiple steps of preinitiation complex assembly.; Nature, 1993 366:531.
Lin et al., Mechanism of action of an acidic transcriptional activator in vitro.; Cell, 1991, 64:971.
Roberts et al., Activator-induced conformational change in general transcription factor TFIIB.; Nature, 1994, 371:717.
Koleske et al., An RNA polymerase II holoenzyme responsive to activators.; Nature, 1994 368:466.
Gill et al., Negative effect of the transcriptional activator GAL4.; Nature, 1988, 334:721.
Ptashne and Gann, Genes & Signals; Cold Spring Harbor Laboratory: New York (2001).
Darnell, Transcription factors as targets for cancer therapy.; Nat. Rev. Cancer, 2002, 2:740.
Duncan et al., Regulation of a Transcription Factor Network Required for Differentiation and Metabolism; Science, 1998, 281:692.
Pandolfi, P. P., Transcription therapy for cancer.; Oncogene, 2001, 20:3116.
Ansari and Mapp, Modular design of artificial transcription factors.; Curr. Opin. Chem. Biol., 2002, 6:765.
Mapp, Regulating transcription: a chemical perspective.; Org. Biomol. Chem., 2003, 1:2217.
Weathermann et al., Chemical approaches to studying transcription.; Org. Biomol. Chem., 2003, 1:3257.
Vasavada et al., A Contingent Replication Assay for the Detection of Protein-Protein Interactions in Animal Cells; Proc. Natl. Acad. Sci. USA, 1991, 88:10686.
Fearon et al., Karyoplasmic Interaction Selection Strategy: A General Strategy to Detect Protein-Protein Interactions in Mammalian Cells; Proc. Natl. Acad. Sci. USA, 1992, 89:7958.
Finkel et al., Detection and modulation in vivo of helix-loop-helix protein-protein interactions; J. Biol. Chem., 1993, 268:5.
Fields et al., The two-hybrid system: an assay for protein-protein interactions.; Trends Genet., 1994, 10:286.
Allen et al., Finding prospective partners in the library: the two-hybrid system and phage display find a match.; Trends Biol. Sci., 1995, 20:511.
Nelson, Structure and function of DNA-binding proteins.; Curr. Op. Genet. Dev., 1995, 5:180.

* cited by examiner

*Primary Examiner*—Sue Liu
(74) *Attorney, Agent, or Firm*—Casimir Jones S.C.

(57) ABSTRACT

The present invention relates to gene regulation. In particular, the present invention provides small molecule activation domain compositions and methods of making the same. The present invention further provides methods of regulating gene expression using the novel activation domains. The invention also provides methods of screening small molecule/compound libraries for identifying ligands of a protein or molecule of interest.

8 Claims, 28 Drawing Sheets

FIGURE 5
a)
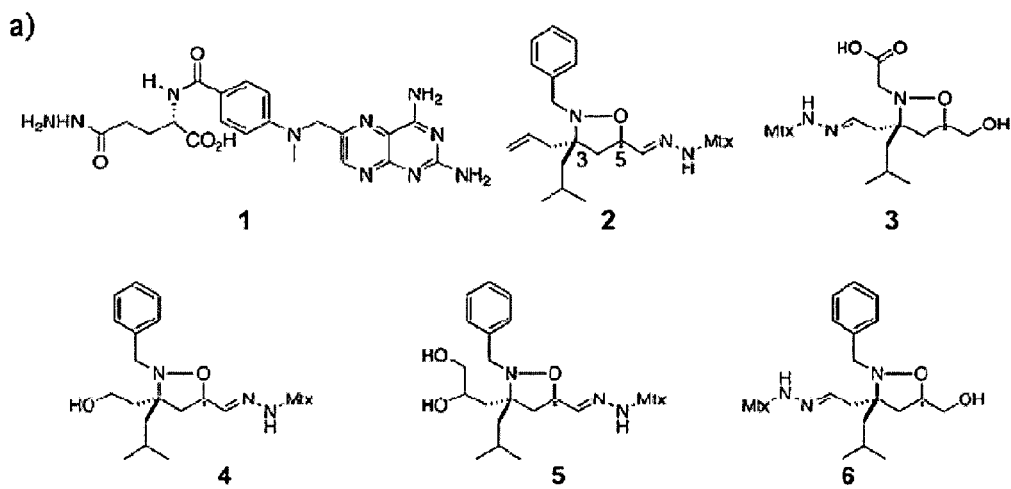
b)
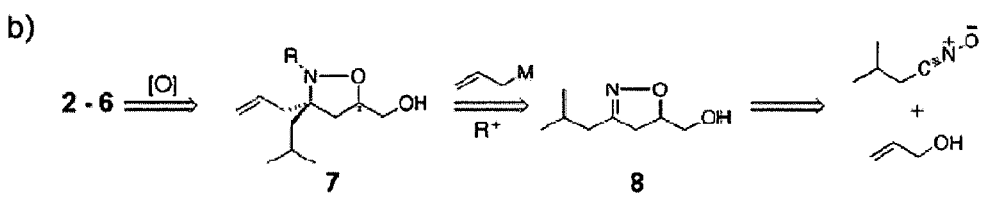
c)
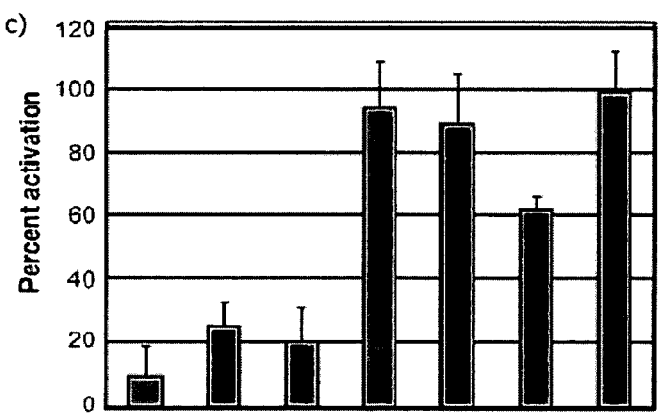
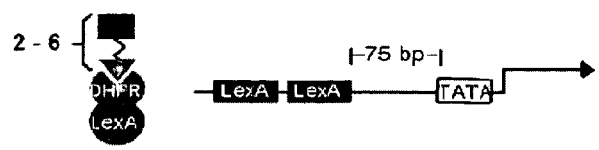

SMALL MOLECULE TRANSCRIPTIONAL ACTIVATION DOMAINS

This application claims priority to provisional patent application Ser. No. 60/625,680, filed on Nov. 5, 2004, which is herein incorporated by reference in its entirety.

FIELD OF THE INVENTION

The present invention relates to gene regulation. In particular, the present invention provides small molecule activation domain compositions and methods of making the same. The present invention further provides methods of regulating gene expression using the novel activation domains. The invention also provides methods of screening small molecule/compound libraries for identifying ligands of a protein or molecule of interest.

BACKGROUND OF THE INVENTION

Gene activation requires interaction of DNA-bound activators with proteins binding near the transcription start site of a gene (See, e.g., Ptashne, Nature 335, 983 (1988)). In eukaryotes, activation of RNA polymerase II genes requires many transcription factors in addition to RNA polymerase. Transcriptional activators have been shown to contact one or another of these transcription factors, including TATA-binding protein (TBP), TBP-associated factors (TAFs), TFIIB, and TFIIH (See, e.g., Roeder, Trends Biochem. Sci. 16, 402 (1991); Zawel et al., Prog. Nucl. Acid Res. Mol. Biol. 44, 67 (1993); Conaway et al., Annu. Rev. Biochem. 62, 161 (1993)). Thus, it has been proposed that transcription initiation involves a multistep assembly process, various steps of which might be catalyzed by activators (See, e.g., Buratowski et al., Cell 56, 549 (1989); Choy et al., Nature 366, 531 (1993)).

Some transcriptional activators are thought to recruit one or more transcription factors to the DNA, to cause crucial conformational changes in target proteins and thereby to facilitate the complex process of assembling the transcriptional machinery, or both (See, e.g., Lin et al., Cell 64, 971 (1991); Roberts et al., Nature 371, 717 (1994); Hori et al., Curr. Op. Genet. Dev. 4, 236 (1994)). Also, given the observation that yeast RNA polymerase II is associated with several transcription factors, in a complex termed the "holoenzyme", it has been proposed that some transcriptional activators might function by recruiting the holoenzyme complex to DNA (See, e.g., Koleske et al., Nature 368, 466 (1994); Kim et al., Cell 77, 599 (1994); Carey, Nature 368, 402 (1994)).

Several difficulties have been encountered in the use and analysis of transcriptional activation systems. For example, over-expression of currently available, protein-based transcriptional activators in cells typically inhibits gene expression, sometimes with dire results on the cells. This effect, termed "squelching", apparently represents the titration of a transcription factor by the over-expressed transcriptional activator (See, e.g., Gill et al., Nature 334, 721 (1988)). Furthermore, over-expression often leads to non-specific activation of multiple genes.

Difficulties and limitations are also encountered using protein-based transcriptional activators in the context of protein-protein interaction applications. For example, useful controls are often unavailable, so that spurious results are frequently observed. Additionally, while "two-hybrid" type assays have provided a tool for detecting and/or characterizing protein-protein interactions, an analogous assay to identify small molecule/compound-protein interactions (i.e., for the discovery of small molecule/compound ligands for specific proteins) is currently not available. Such an assay would be an enormously powerful tool for rapidly identifying ligands for specific proteins in the context of the cell, important for pharmaceutical applications as well as for basic research.

Given that transcriptional activators represent a significant fraction of all known proteins, these limitations present serious hurdles in basic research and clinical therapeutics.

Hence, a need exists for the identification of novel transcriptional activators. In particular, there is a need for synthetic transcriptional activators that target the activation of specific genes without "squelching" other known activators, for methods of regulating the expression of specific genes without randomly activating other genes, and for methods of screening small molecule/compound libraries to identify protein ligands of a protein of interest.

SUMMARY OF THE INVENTION

The present invention relates to gene regulation. In particular, the present invention provides small molecule activation domain compositions and methods of making the same. The present invention further provides methods of regulating gene expression using the novel activation domains. Finally, the invention provides methods of screening small molecule/compound libraries for identifying ligands of a protein of interest.

Accordingly, in some embodiments, the present invention provides a composition comprising a transcriptional activation domain comprising an isoxazolidine. In some embodiments, the isoxazolidine comprises a functional group. In some embodiments, the functional group comprises a polar group. In some embodiments, the polar group comprises a hydroxyl group and/or a carboxylic acid group. In some embodiments, the functional group comprises a hydrophobic group. In some embodiments, the hydrophobic group comprises a phenyl group and/or an isobutyl group. In some embodiments, the functional group is located at the N2, C3 or C5 position of the isoxazolidine. In preferred embodiments, the isoxazolidine is:

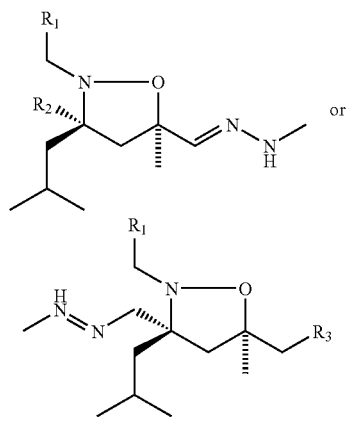

In some embodiments, R1 is a phenyl or $CO_2H$. In some embodiments, R2 is an allyl,

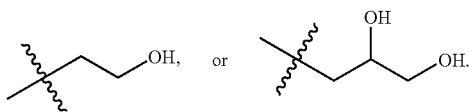

In some embodiments, R3 is OH. In some embodiments, the activation domain is selected from the group comprising:

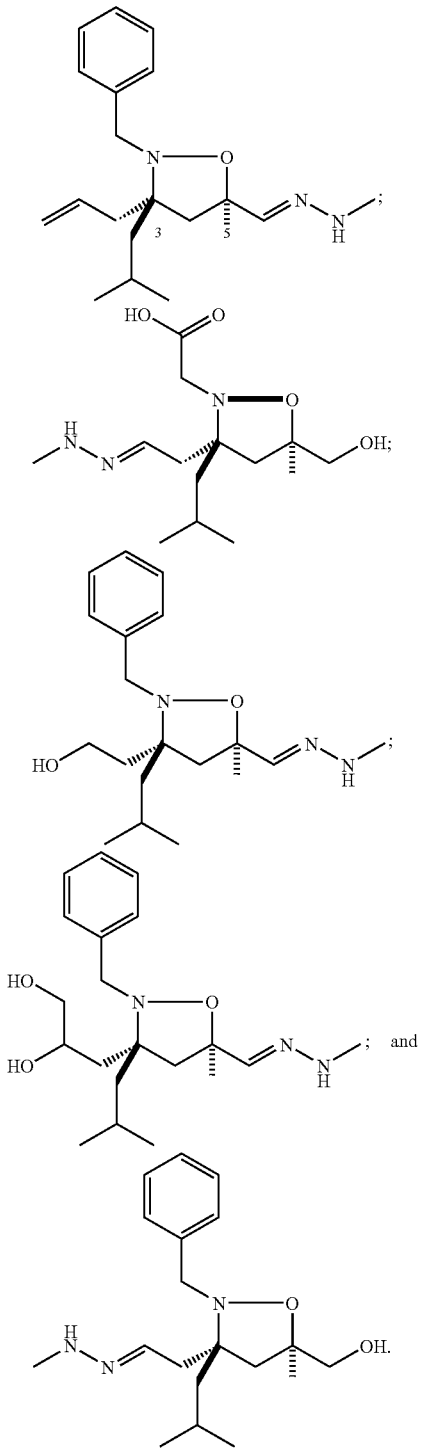

In some embodiments, the isoxazolidine is oligomerized. In some embodiments, the activation domain is fused to a DNA binding domain. In further embodiments, the DNA binding domain is specific for a promoter region in a gene. The present invention is not limited by the nature of the DNA binding domain nor is it limited to a particular gene. In some embodiments, the gene is selected from the group comprising, but not limited to, abl, Bcl-2, Bcl-xL, erb, fms, gsp, hst, jun, myc, neu, raf, ras, ret, src, trk, BRCA1, BRCA2, C-CAM, p16, p21, p53, p73, Rb, and p27, KDR, Renin, C-raf, NOS, NOS(I), ERK7, MAPK, Fms-TK, PKC-α, PKC-α1, PKC-β, SAPK-α, CDK2, Chp-JNK, Ha-ras, C-fos, bcl-2, NF-κB, Cyclin-E AP-1, c-Fos, c-Jun, NF-E2, CRE-BP1, ATF, CREB, C/EBP, NF-IL6, MyoD, E2F, USF, NF-1, RF-X, CP1, ER, GR, PR, RAR, RXR, T3R, COUP, GATA-1, Sp1, YY1, GAL4, EN, HNF-1, OCT, HNF-3, c-Myb, Ets, IRF-1, G3PDH, N/K ATPase, Ca-ATPase, IL-1β, IL-5, IL-6, IL-4, IFN-γ, MIP-1α, MIP-2, MCP-1, RANTES, TNF-α, TNF-αR1, TGF-β, and TGF-βR1.

In some embodiments, the activation domain is coupled to a compound. In some embodiments, the compound is selected from a compound library comprising a plurality of compounds. The present invention is not limited by the nature of compounds. In some embodiments, the compound libraries, comprising putative ligands, are composed of compounds selected from the group consisting of, but not limited to, carbohydrates, monosaccharides, oligosaccharides, polysaccharides, amino acids, peptides, oligopeptides, polypeptides, proteins, nucleosides, nucleotides, oligonucleotides, polynucleotides, lipids, retinoids, steroids, glycopeptides, glycoproteins, proteoglycans, and synthetic small molecule organic compounds.

The invention also provides a method of making an activation domain, comprising preparing and purifying an isoxazolidine; conjugating a functional group to the isoxazolidine, wherein the functional group comprises a hydrophobic and a polar group, the conjugating comprising controlling the stereochemistry at the C3 and C5 positions via addition of an allyl Grignard to the isoxazolidine; alkylation of N2 to introduce a benzyl or acidic group at the N2 position; and hydrazone formation permitting conjugating the isoxazolidine to a DNA binding domain, to a small molecule/compound, to itself or another isoxazolidine.

The present invention also provides a method of screening a compound library to identify ligands of a protein of interest, comprising providing the protein of interest fused to a DNA binding domain, a small molecule activation domain coupled to a compound library comprising a plurality of compounds, and host cells containing a reporter gene; combining the protein of interest, the small molecule activation domain coupled to the compound library, and the host cells under conditions such that the protein of interest is able to interact with the plurality of compounds; detecting the interaction under conditions such that the activation of the reporter gene is measured; and determining the identification of the ligand. In some embodiments, the compound library comprises less than about 10,000 putative ligands. In some embodiments, the compound library comprises about 5 to about 100 putative ligands. In some embodiments the host cells are bacterial, yeast or mammalian cells.

The present invention also provides a kit for identifying small molecule ligands of a protein of interest, comprising a plasmid for generating a DNA binding domain fused to said protein of interest; a small molecule activation domain; and host cells containing a reporter gene. In some embodiments, the small molecule activation domain is pre-activated for conjugation to a compound library comprising a plurality of compounds. In some embodiments, the pre-activation of the small molecule activation domain comprises chemical synthesis of the composition described above under conditions such that the composition behaves as an electrophile or nucleophile. (e.g., formation of an aldehyde, thiol or amine intermediate).

The invention also provides a method for screening a plurality of compound libraries to determine the relative affinity of putative ligands in each library to a protein of interest, comprising providing a plurality of compound libraries, each library comprising a plurality of putative ligands; a protein of interest fused to a DNA binding domain specific for a promoter region of a reporter gene; coupling the compound libraries to a small molecule activation domain; providing host cells containing the reporter gene and the protein of interest fused to the DNA binding domain; combining the coupled compound libraries and the host cells under conditions such that the protein of interest is able to interact with the compound libraries; detecting the interaction under conditions such that the activation of the reporter gene is measured; and determining the identification of the ligand.

The invention also provides a method of regulating expression of a gene of interest comprising providing host cells and a small molecule activation domain fused to a DNA binding domain, and delivering to the host cells an effective amount of the small molecule activation domain fused to a DNA binding domain such that expression of the gene of interest is modulated. The modulation of expression can be, for example, repression or activation. In some embodiments, the host cells may be isolated, in culture, ex vivo, in tissue or in vivo.

The present invention also provides a method of regulating expression of a gene of interest in a subject, comprising providing a subject and a small molecule activation domain fused to a DNA binding domain and delivering to the subject an effective amount of the small molecule activation domain fused to a DNA binding domain such that expression of the gene of interest is modified. In some embodiments, the subject is human.

The present invention also provides a method of treatment, comprising providing a subject with a symptom of disease, a therapeutic formulation comprising a small molecule activation domain fused to a DNA binding domain, and administering the formulation to the subject under conditions such that the symptom is reduced.

DESCRIPTION OF THE DRAWINGS

FIG. 5 depicts a) isoxazolidine based activation domains bearing functional groups; b) synthetic strategy used to prepare isoxazolidines; and c) results from in vitro transcription assays utilizing the activation domains.

B) reverse-phase HPLC of methotrexate hydrazide/isoxazolidine condensation to form 4-((3RS, 5RS)-3-Allyl-2-benzyl-3-isobutyl-isoxazolidin-5-ylmethylenehydrazinocarbonyl)-2-(4({(6-(amino-methylcarbaminidoylimino-methyl)-pyrazin-2-ylmethyl)-methyl-amino}-methyl)-benzoylamino)-(S)-butyric acid at 18 h; and C) analytical reverse-phase HPLC of methotrexate hydrazide/isoxazolidine condensation to form 4-((3RS, 5RS)-3-Allyl-2-benzyl-3-isobutyl-isoxazolidin-5-ylmethylenehydrazinocarbonyl)-2-(4({(6-(amino-methylcarbaminidoylimino-methyl)-pyrazin-2-ylmethyl)-methyl-amino}-methyl)-benzoylamino)-(S)-butyric acid after isolation (with inset UV scan from 250-500 nm).

Figure 10:
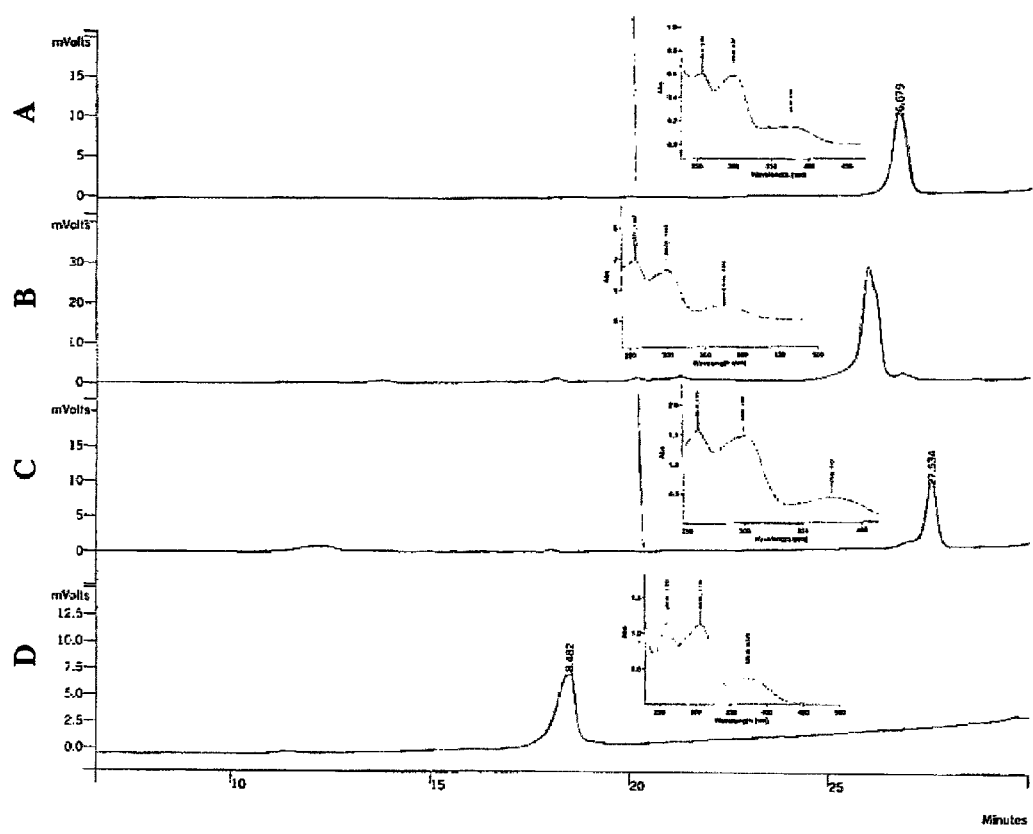

FIG. 10 depicts analytical reverse-phase HPLC of:
A) 2-(4({(6-(Amino-methylcarbaminidoylimino-methyl)-pyrazin-2-ylmethyl)-methylamino}-methyl)-benzoylamino)-4-(2-benzyl-(3RS)-(2-hydroxy-ethyl)-3-isobutylisoxazolidin-(5RS)-ylmethylene-hydrazinocarbonyl)-(S)-butyric acid after isolation (with inset UV scan from 250-500 nm);

B) 2-(4({(6-(Amino-methylcarbaminidoylimino-methyl)-pyrazin-2-ylmethyl)-methylamino}-methyl)-benzoylamino)-4-(2-benzyl-(3RS)-(3-hydroxy-2-methoxy-propyl)-(3RS)-isobutyl-isoxazolidin-(5RS)-ylmethylene-hydrazinocarbonyl)-(S)-butyric acid after isolation (with inset UV scan from 250-500 nm);

C) 2-(4({(6-(Amino-methylcarbaminidoylimino-methyl)-pyrazin-2-ylmethyl)-methylamino}-methyl)-benzoylamino)-4-(2-(2-benzyl-(5RS)-hydroxymethyl-(3RS)-isobutylisoxazolidin-3-yl)-ethylidene-hydrazinocarbonyl)-(S)-butyric acid after isolation (with inset UV scan from 250-500 nm); and D) Mtx-ATF-14 after isolation (with inset UV scan from 250-500 nm).

Figure 11A:
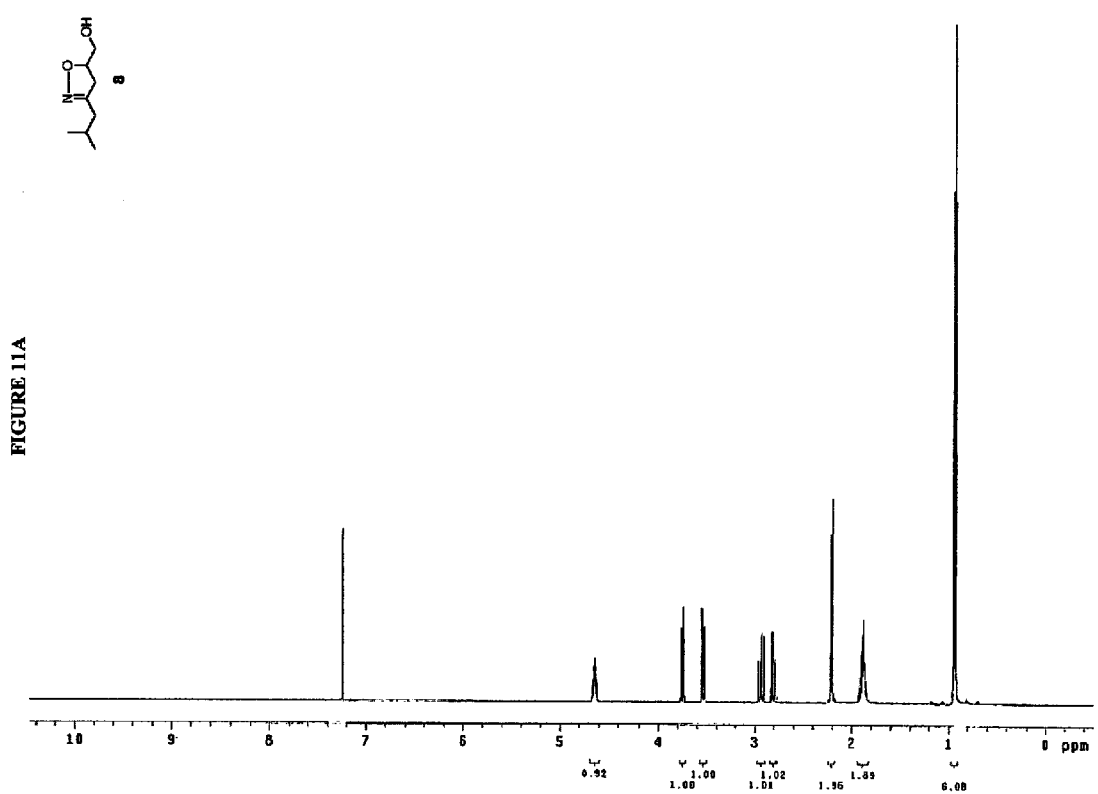

FIG. 11A depicts NMR spectra displaying purity of (3-Isobutyl-4,5-dihydro-isoxazol-5-yl)-methanol.

Figure 11B:
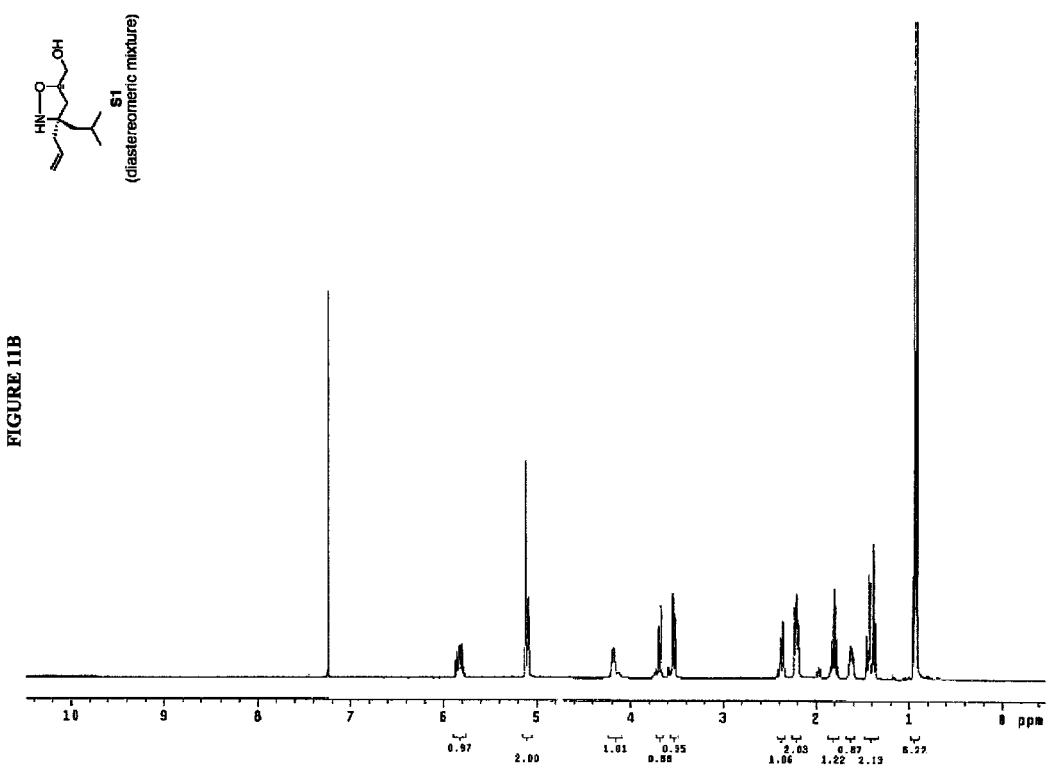

FIG. 11B depicts NMR spectra displaying purity of (3-Allyl-3-isobutyl-isoxazolidin-5-yl)-methanol.

Figure 11C:
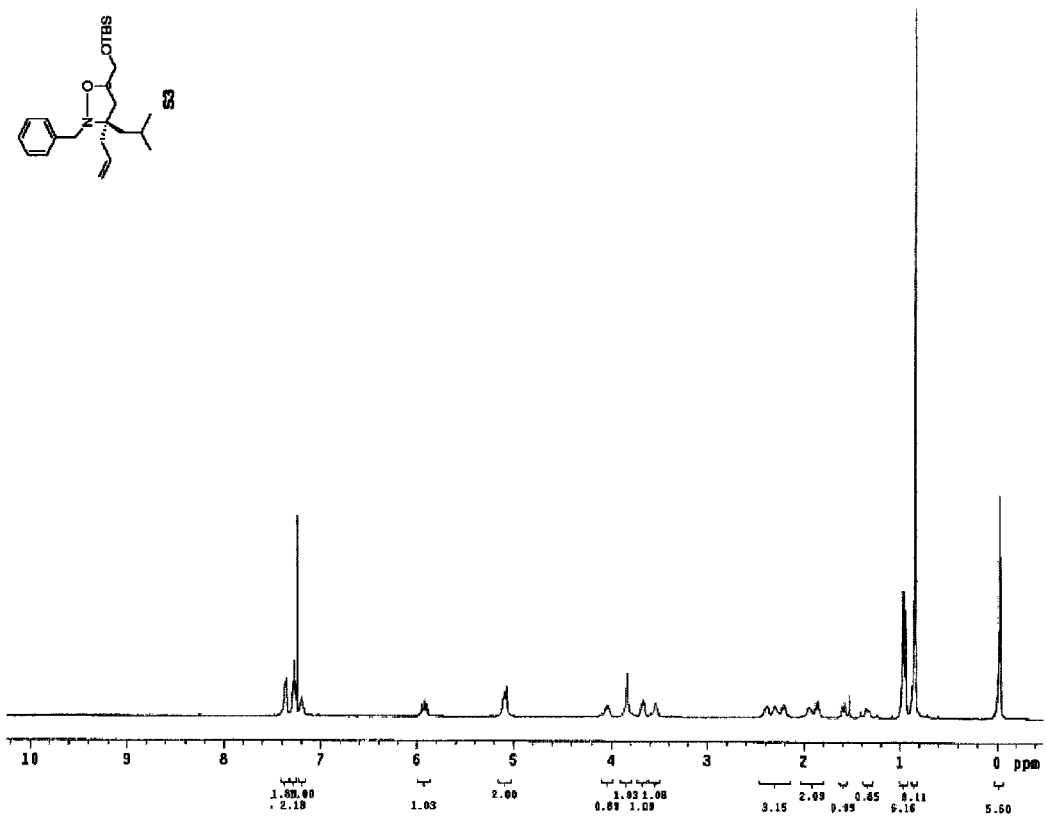

FIG. 11C depicts NMR spectra displaying purity of 3-Allyl-2-benzyl-5-(tert-butyl-dimethyl-silanyloxymethyl)-3-isobutyl-isoxazolidine.

Figure 11D:
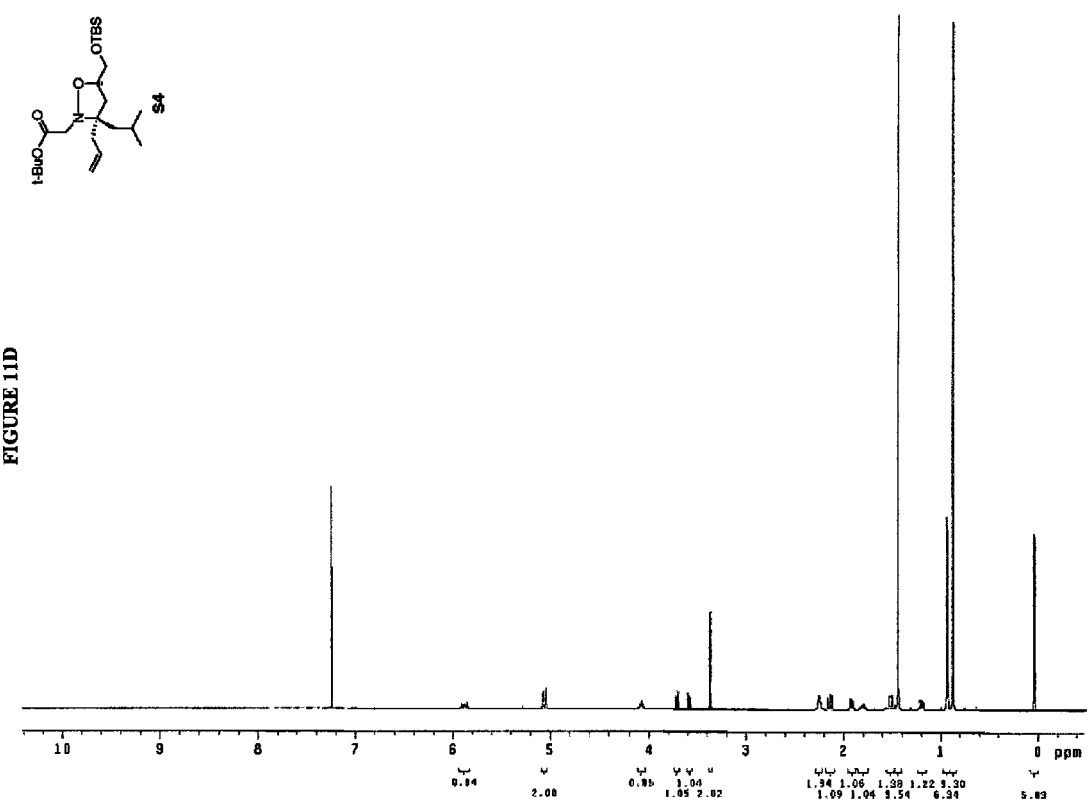

FIG. 11D depicts NMR spectra displaying purity of (3-Allyl-5-(tert-butyl-dimethyl-silanyloxymethyl)-3-isobutyl-isoxazolidin-2-yl)-acetic acid tert-butyl ester.

Figure 11E:
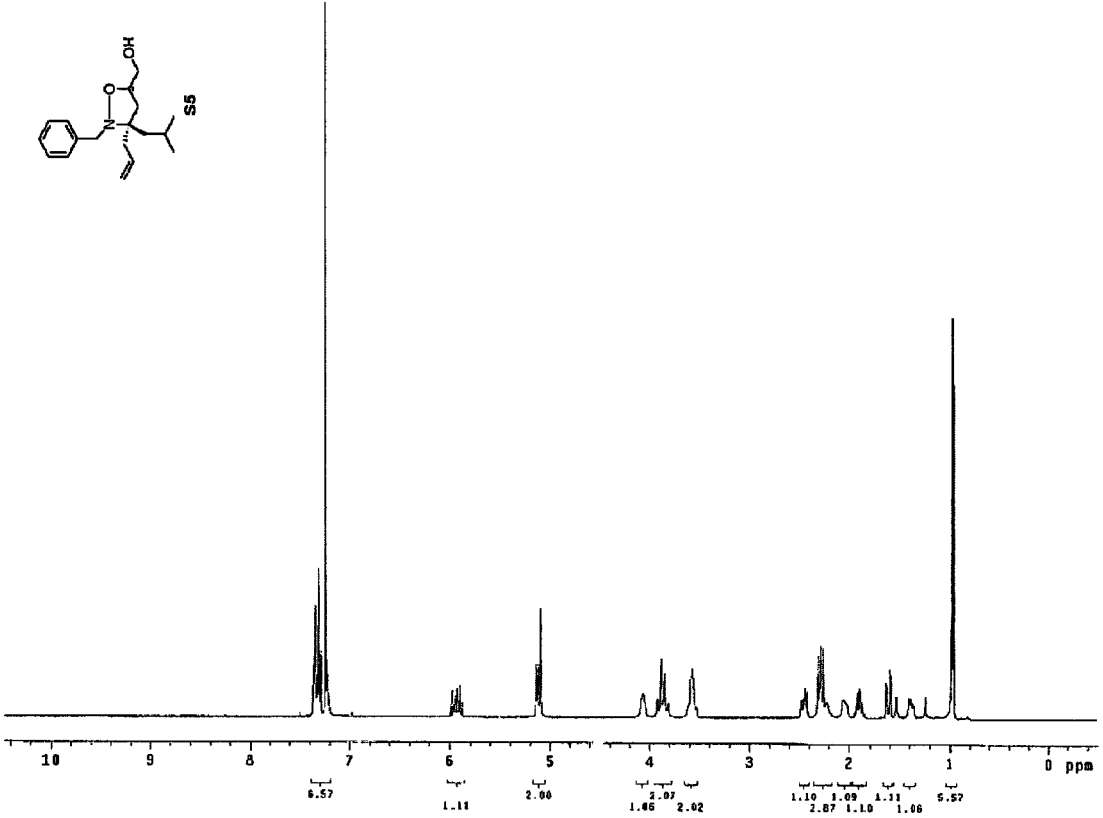

FIG. 11E depicts NMR spectra displaying purity of (3-Allyl-2-benzyl-3-isobutyl-isoxazolidin-5-yl)-methanol.

Figure 11F:
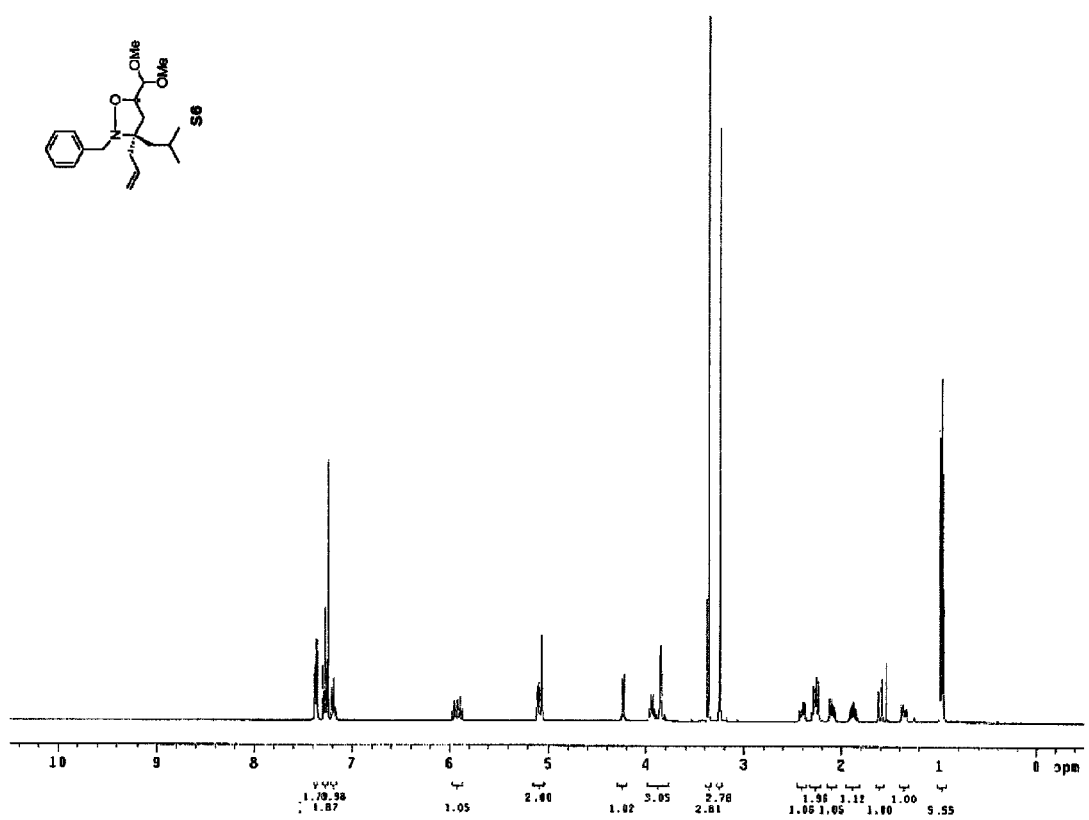

FIG. 11F depicts NMR spectra displaying purity of 3-Allyl-2-benzyl-5-dimethoxymethyl-3-isobutyl-isoxazolidine.

Figure 11G:
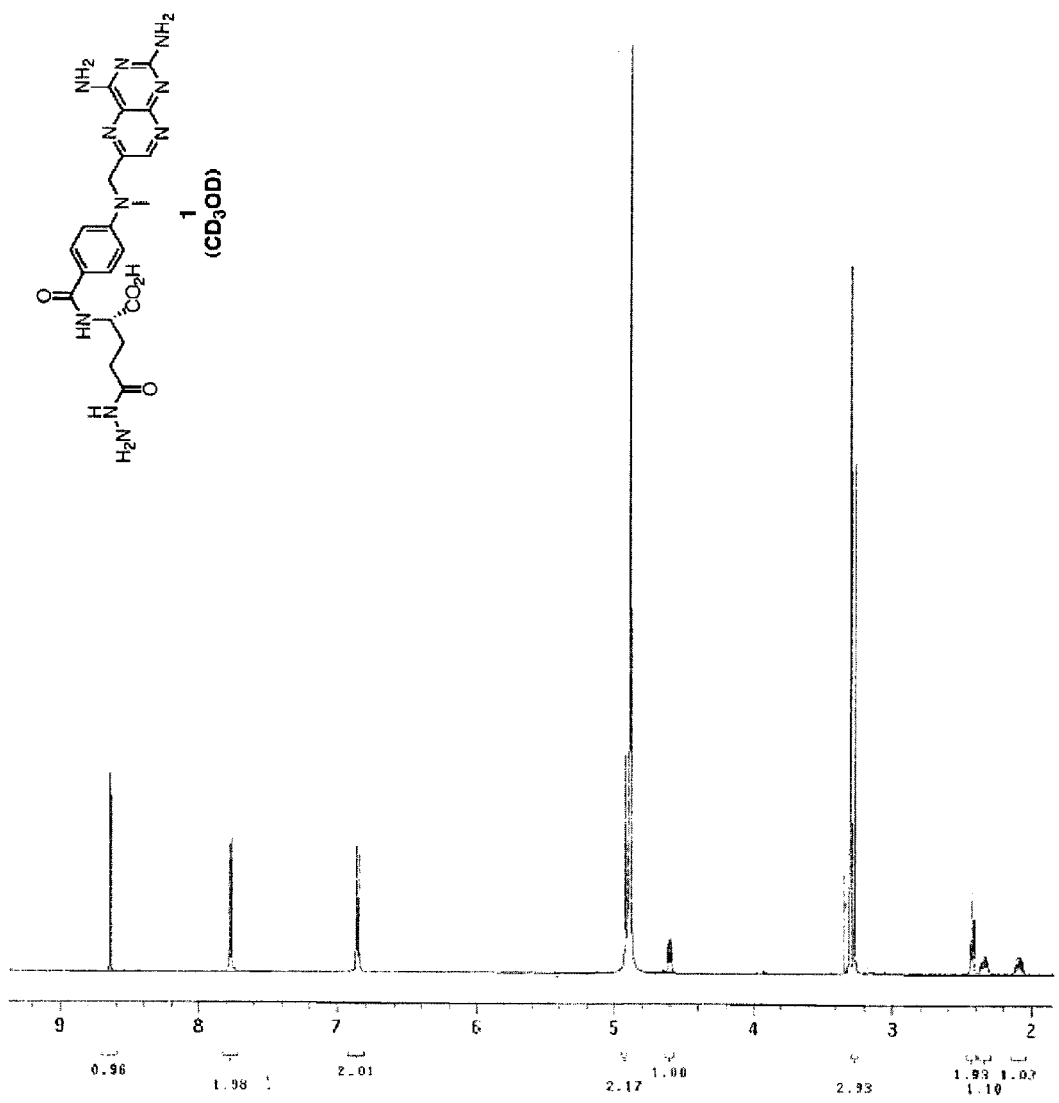

FIG. 11G depicts NMR spectra displaying purity of 2-{4-((2,4-diamino-pteridin-6-ylmethyl)-methyl-amino)-benzoylamino}-4-hydrazinocarbonyl-(S)-butyric acid.

Figure 11H:
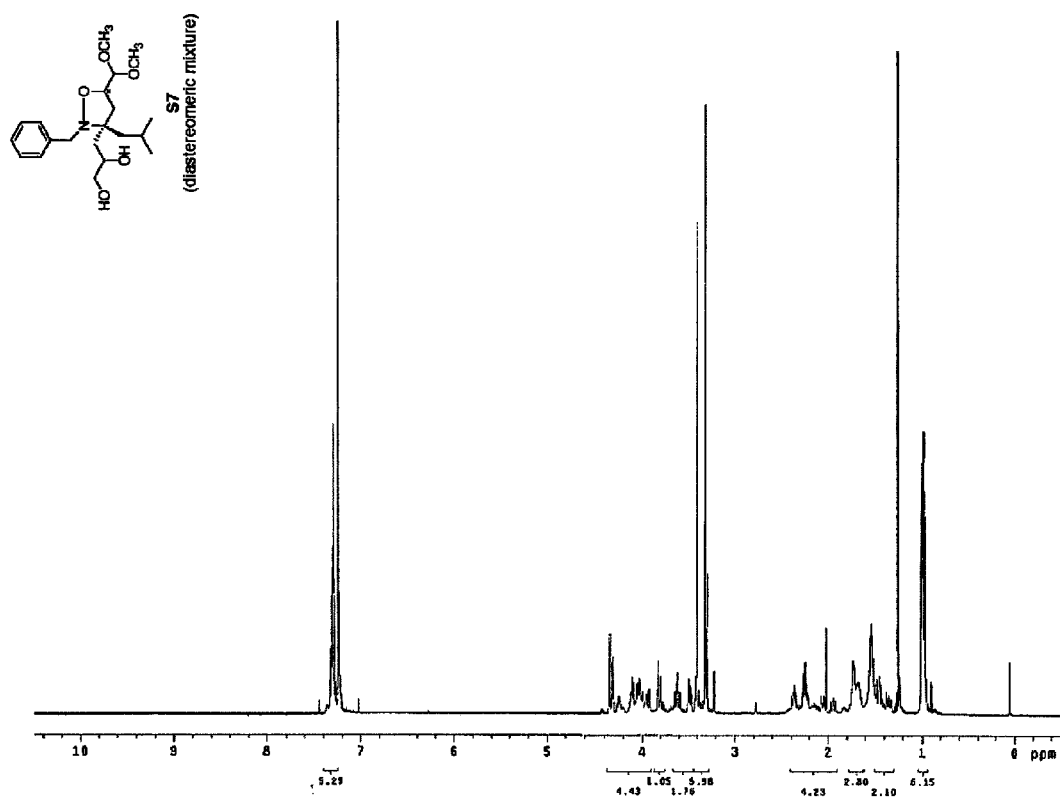

FIG. 11H depicts NMR spectra displaying purity of 3-(2-Benzyl-5-dimethoxymethyl-3-isobutyl-isoxazolidin-3-yl)-propane-1,2-diol.

Figure 11I:
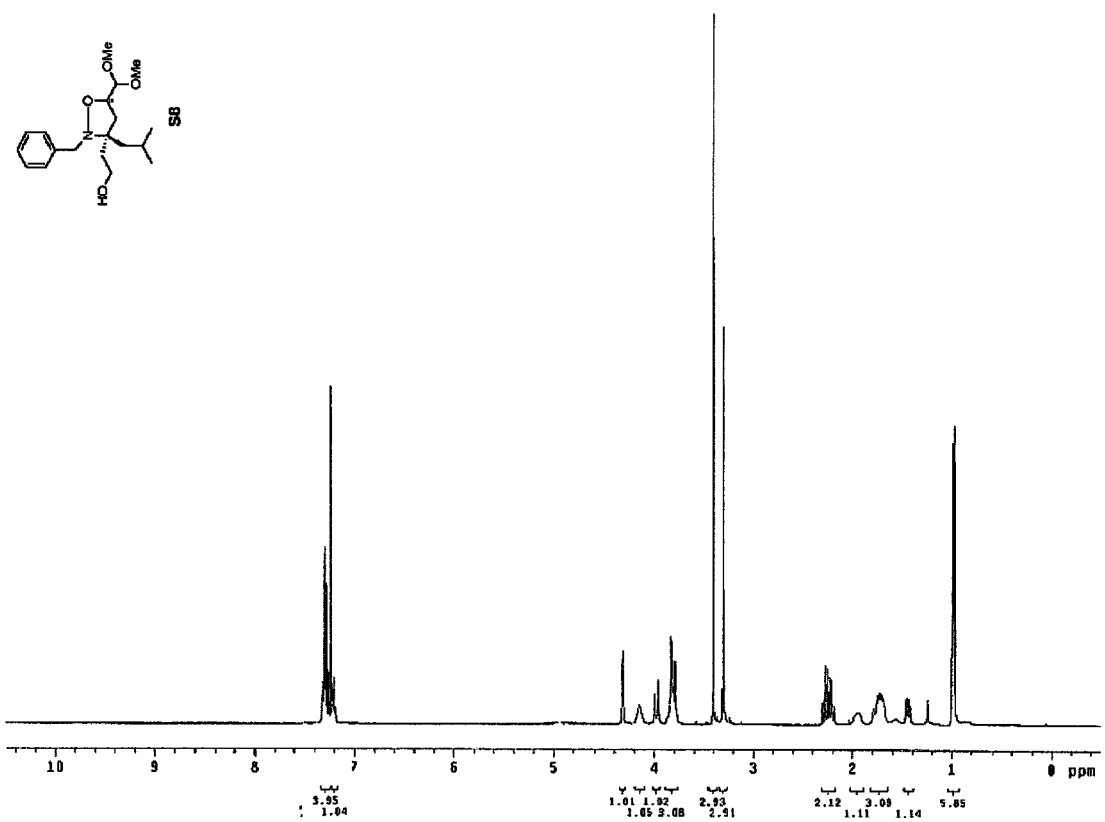

FIG. 11I depicts NMR spectra displaying purity of 2-(2-Benzyl-5-dimethoxymethyl-3-isobutyl-isoxazolidin-3-yl)-ethanol.

Figure 11J:
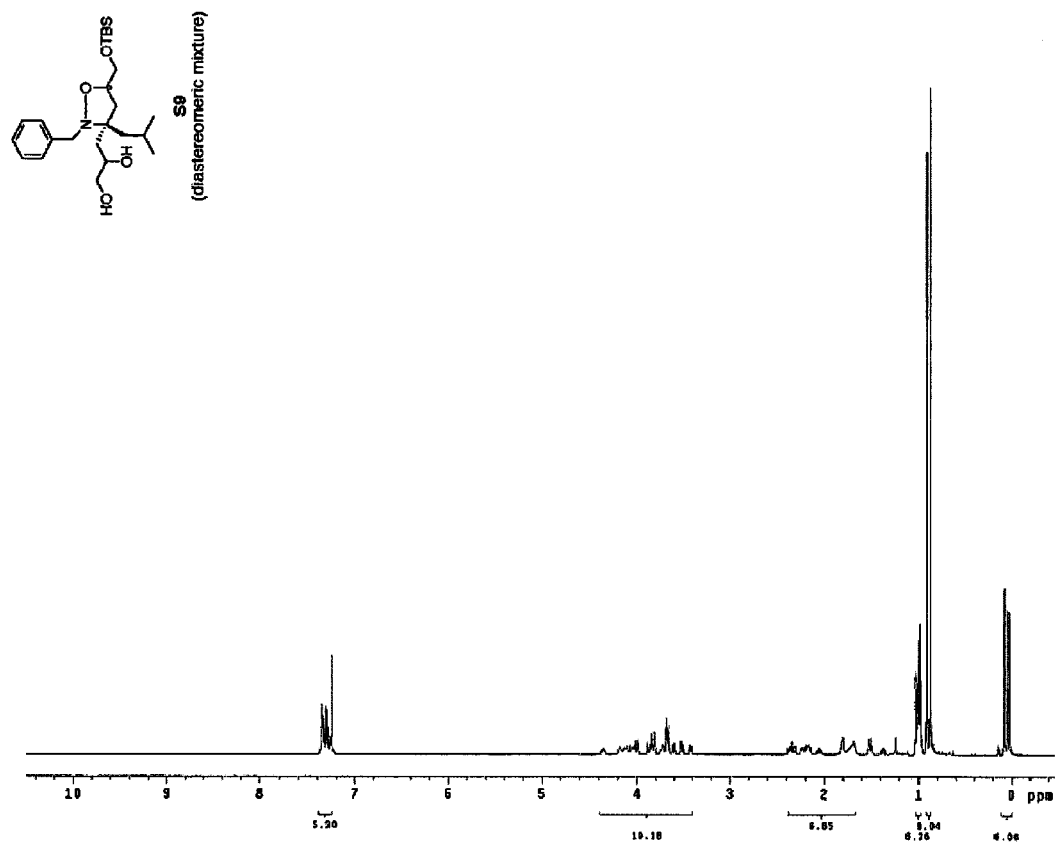

FIG. 11J depicts NMR spectra displaying purity of 3-(2-Benzyl-5-(tert-butyl-dimethyl-silanyloxymethyl)-3-isobutyl-isoxazolidin-3-yl)-propane-1,2-diol.

Figure 11K:
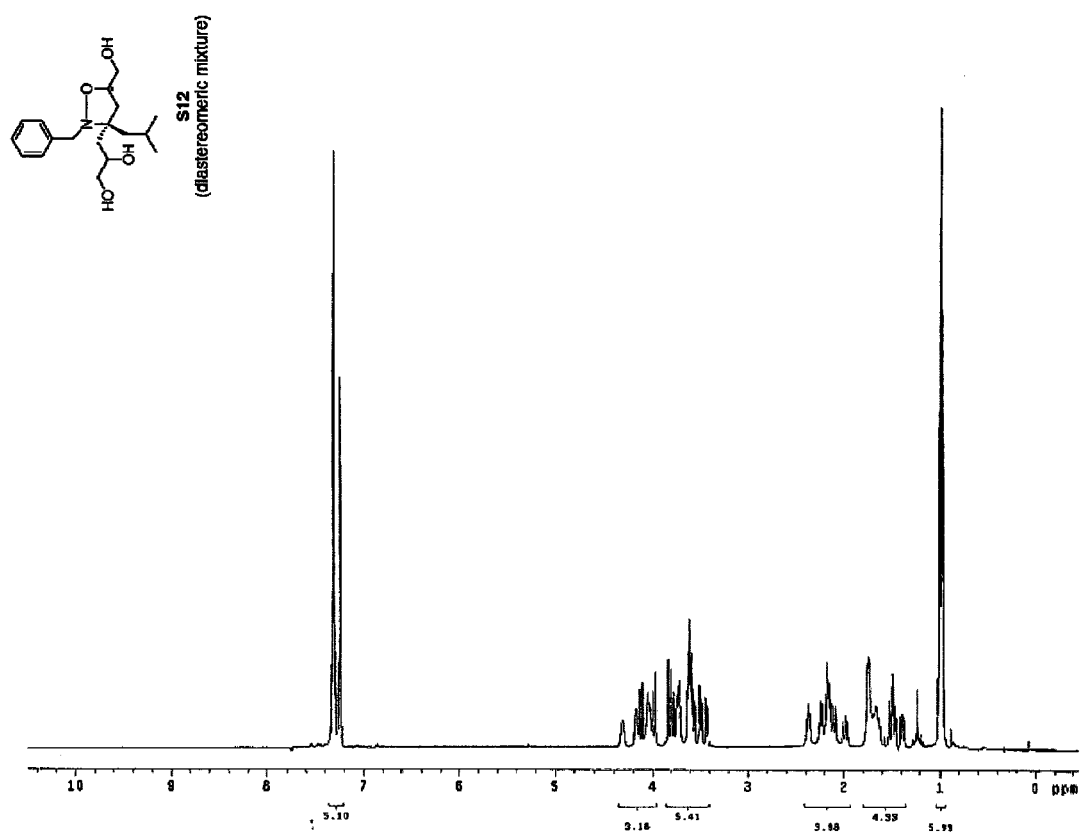

FIG. 11K depicts NMR spectra displaying purity of 3-(2-Benzyl-5-hydroxymethyl-3-isobutyl-isoxazolidin-3-yl)-propane-1,2-diol.

Figure 11L:
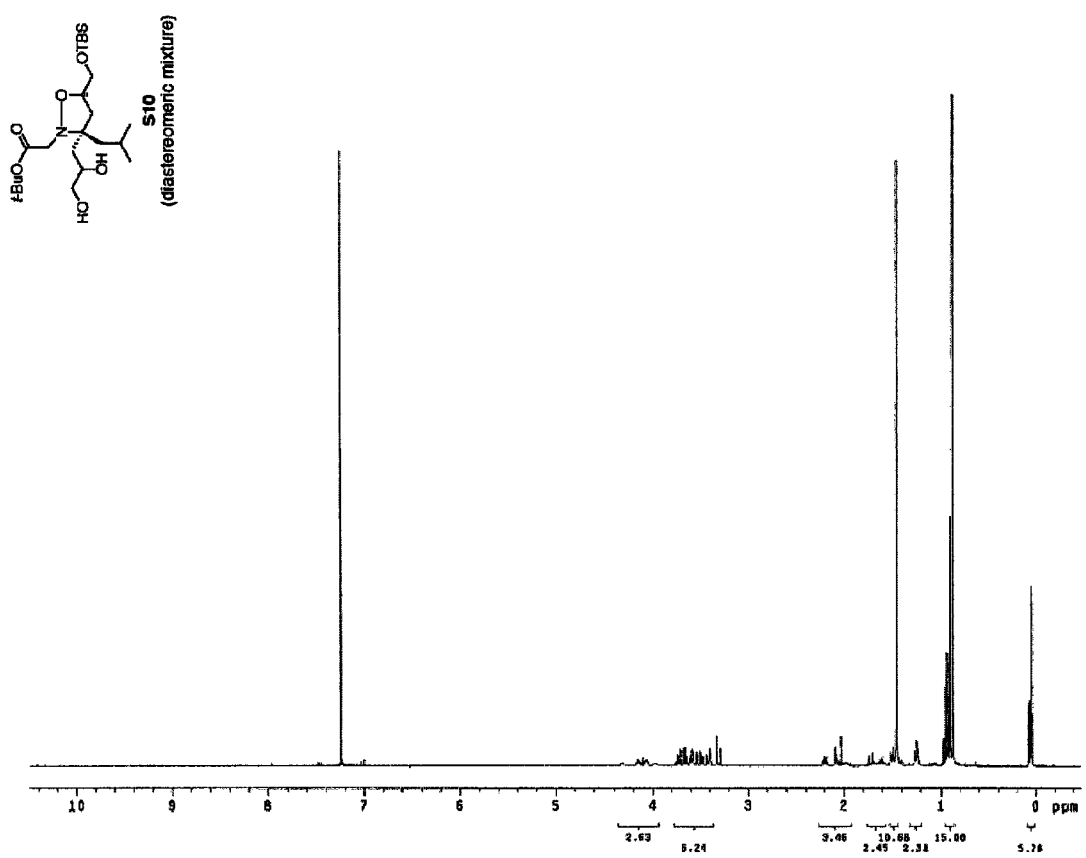

FIG. 11L depicts NMR spectra displaying purity of (5-(tert-Butyl-dimethyl-silanyloxymethyl)-3-(2,3-dihydroxy-propyl)-3-isobutylisoxazolidin-2-yl) acetic acid tert-butyl ester.

Figure 11M:
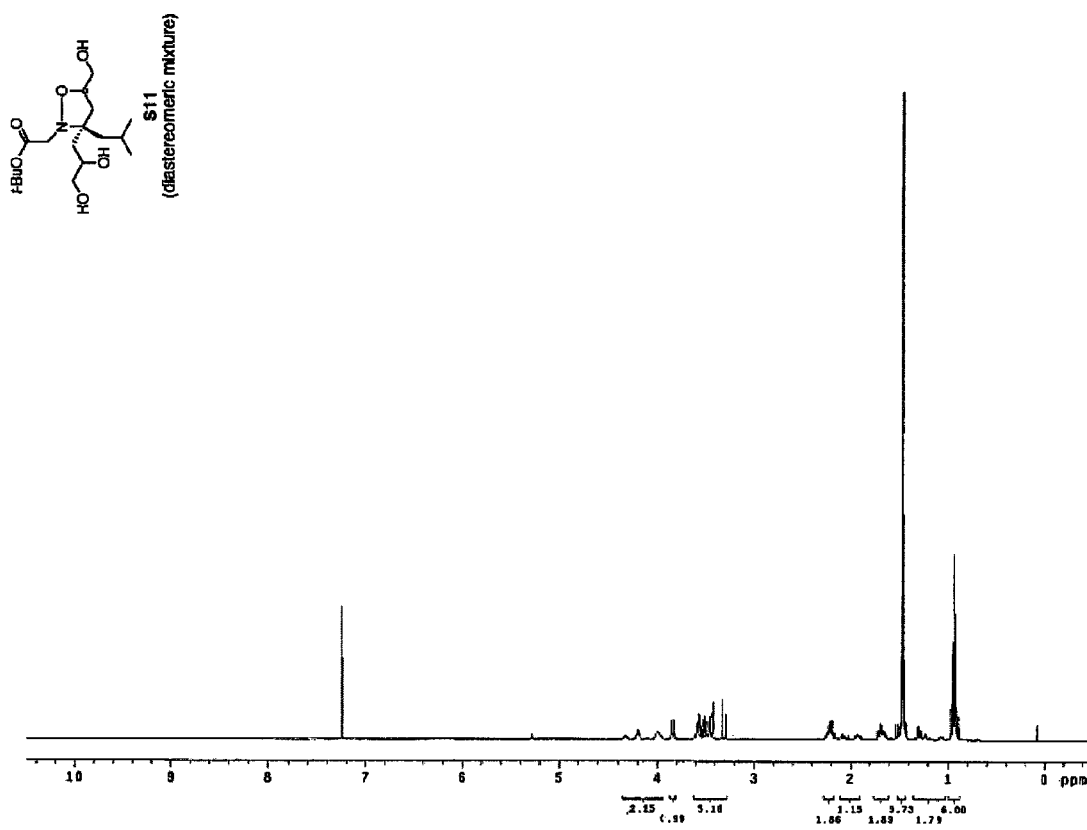

FIG. 11M depicts NMR spectra displaying purity of (3-(2, 3-dihydroxy-propyl)-5-hydroxymethyl-3-isobutyl-isoxazolidin-2-yl)acetic acid tert-butyl ester.

Figure 12:
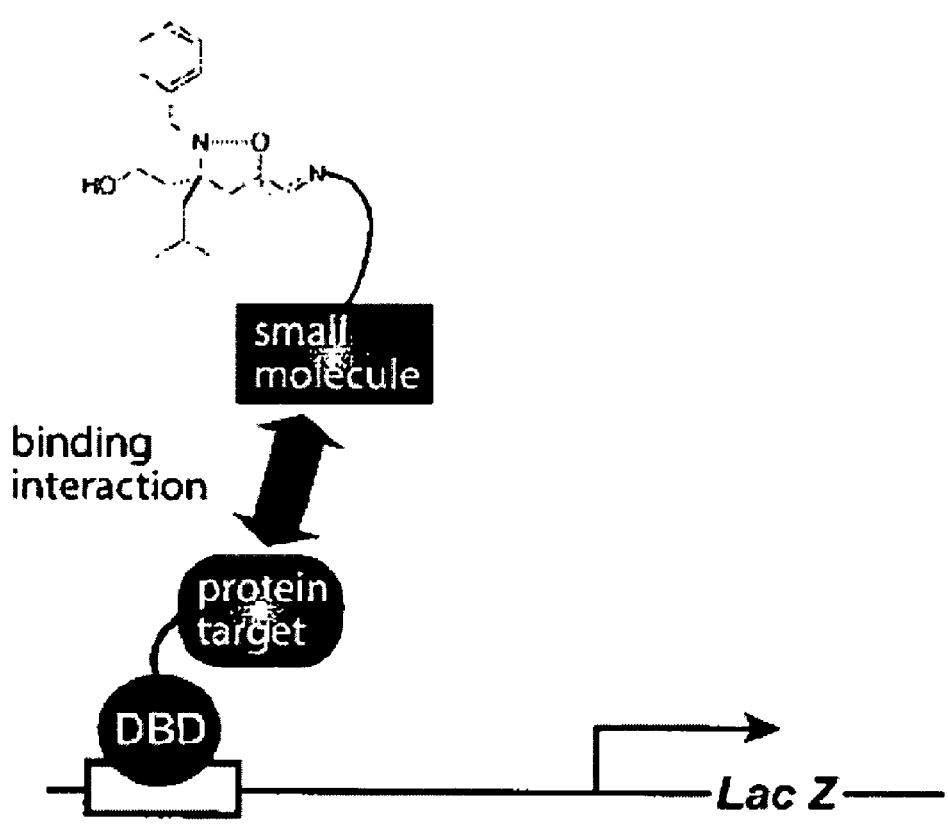

FIG. 12 depicts a rapid screen/assay for identification of ligands for a protein of interest.

Figure 13:
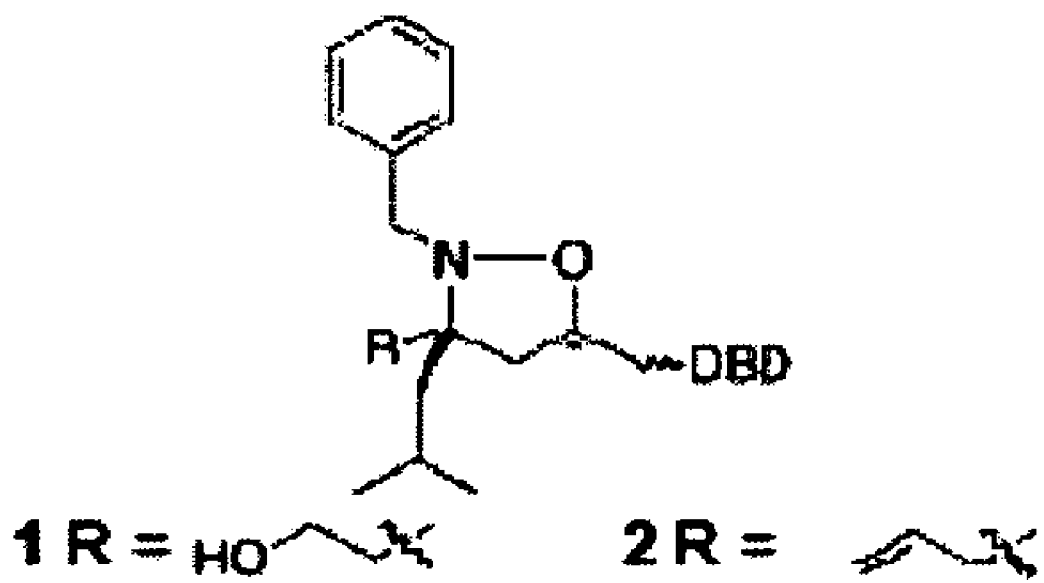

FIG. 13 depicts a small molecule activation domain 1 of the present invention.

Figure 14:
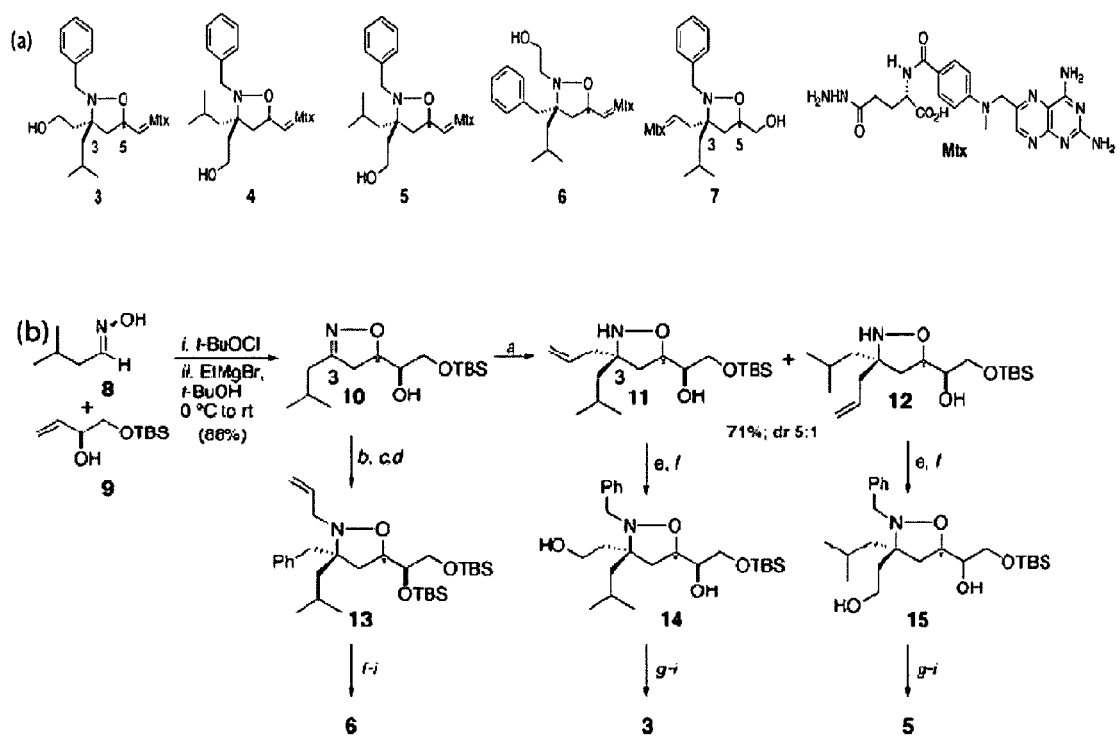

FIGS. 14a and 14b depict isoxazolidines with varying spatial orientations of polar and hydrophic functional groups of the present invention.

Figure 15:
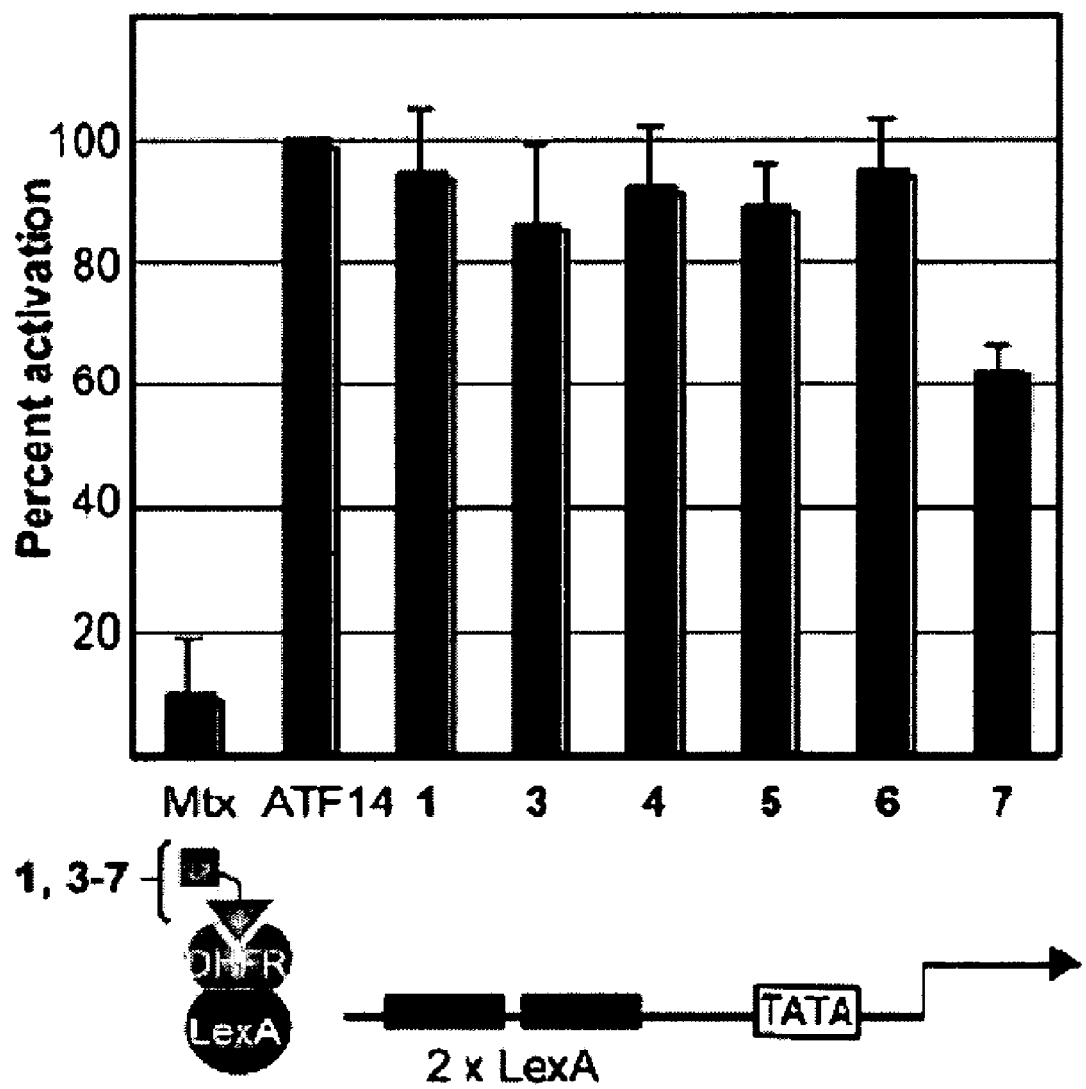

FIG. 15 shows results from in vitro transcription assays.

Figure 16:
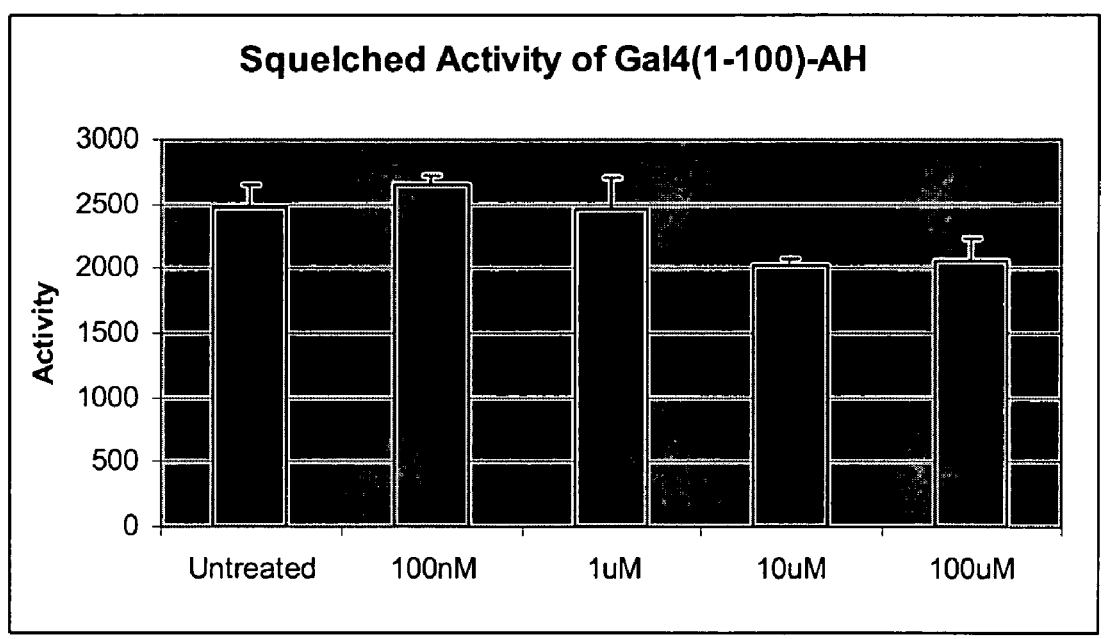

FIG. 16 shows that small molecule activation domains of the present invention function to inhibit endogenous transcriptional activation domains.

DEFINITIONS

The term "small molecule/compound library" refers to a mixture or collection of one or more putative ligands generated or obtained in any manner. Preferably, the library contains more than one putative ligand or member. The term "ligand" refers to a molecule/compound or group of molecules/compounds that bind to one or more specific sites of a protein of interest. Representative small molecules/compounds include, by way of illustration, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like, and synthetic analogues or derivatives thereof, including peptidomimetics, small molecule organic compounds and the like, and mixtures thereof. The term "putative ligand" refers to a ligand whose affinity or specificity for a protein of interest, if any, has not been determined.

The small molecule/compound libraries employed in this invention may be prepared or obtained by any means including, but not limited to, combinatorial chemistry techniques, fermentation methods, plant and cellular extraction procedures and the like. Methods for making combinatorial libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Each of these references is incorporated herein by reference in its entirety.

A particular advantage of the present method is that compound libraries containing racemic mixtures may be screened to determine, for example, if only one isomer (e.g. an enantiomer or diastereomer) is binding to the protein of interest, or if the isomers have different affinities for the protein of interest. In this regard, if the isomers have different affinities for the protein of interest, a different level of reporter activation will observed for each isomer.

The compound libraries employed in this invention will typically contain a plurality of members or putative ligands. When an indicator compound is employed, the compound library will preferably contain less than about 50,000 members, more preferably, the compound library will contain less than about 10,000 members. When an indicator compound is not employed, the compound library will preferably contain less than about 10,000 members; more preferably, from 1 to about 1,000 members; and still more preferably, from about 5 to about 100 members.

The term "synthetic small molecule organic compounds" refers to organic compounds generally having a molecular weight less than about 1000, preferably less than about 500, which are prepared by synthetic organic techniques, such as by combinatorial chemistry techniques.

The term "host cell" or "cell" refers to any cell which is used in any of the methods (e.g., screening assay or regulation of gene expression) of the present invention and may include prokaryotic cells, eukaryotic cells, yeast cells, bacterial cells, plant cells, animal cells, such as, reptilian cells, bird cells, fish cells, mammalian cells. Preferred cells include those derived from humans, dogs, cats, horses, cattle, sheep, pigs, llamas, gerbils, squirrels, goats, bears, chimpanzees, mice, rats, rabbits, etc. The term cells includes transgenic cells from cultures or from transgenic organisms. The cells may be from a specific tissue, body fluid, organ (e.g., brain tissue, nervous tissue, muscle tissue, retina tissue, kidney tissue, liver tissue, etc.), or any derivative fraction thereof. The term includes healthy cells, transgenic cells, cells affected by internal or exterior stimuli, cells suffering from a disease state or a disorder, cells undergoing transition (e.g., mitosis, meiosis, apoptosis, etc.), etc. The term also refers to cells in vivo or in vitro (e.g., the host cell may be located in a transgenic animal or in a human subject).

The term "pre-activated" refers to chemical manipulation of a moiety such that it exists in a ready state to be conjugated with another moiety. In some embodiments, an activation domain of the present invention is pre-activated through chemical synthesis (e.g., chemical steps to produce an aldehyde, thiol or an amine) such that the activation domain behaves as an electrophile or a nucleophile.

The term "coupled to," "conjugated" and "fused to" refers to means of attaching an activation domain of the present invention to another moiety. In some embodiments, the activation domain is conjugated to a small molecule/compound. In some embodiments, the activation domain is conjugated to itself. In still other embodiments, the activation domain is conjugated to a DNA binding domain. Such attachment may be through covalent, ionic, hydrogen or Van der Waals interactions, or may be through the use of a linking agent. Linkers may include peptide or synthetic sequences and are well known to those of skill in the art.

As used herein, the terms "host" and "subject" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, aves, etc.), that is studied, analyzed, tested, diagnosed or treated. As used herein, the terms "host" and "subject" are used interchangeably.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The term "promoter region" refers to the 5' flanking region of a gene and may contain regulatory sequences such as promoters and enhancers that control or influence the transcription of the gene. The 3' flanking region may contain sequences that direct the termination of transcription, post-transcriptional cleavage and polyadenylation.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horseradish peroxidase.

As used herein, the term "oligomerized" refers to compositions wherein two or more activation domains are conjugated to each other.

DETAILED DESCRIPTION OF THE INVENTION

The present invention relates to gene regulation. In particular, the present invention provides small molecule activation domain compositions and methods of making the same. The present invention further provides methods of regulating gene expression using the novel activation domains. Finally, the invention provides methods of screening small molecule/compound libraries for identifying ligands of a protein or molecule of interest.

Transcriptional activators play an essential role in the regulatory network that controls gene-specific transcription (See, e.g., Ptashne and Gann, Genes & Signals; Cold Spring Harbor Laboratory: New York (2001)). The misregulation of this complex event cascade is correlated with a growing number of human diseases (See, e.g., Darnell Nat. Rev. Cancer 2, 740 (2002); Duncan et al., Science 281, 692 (1998); and Pandolfi, P. P. Oncogene 20, 3116 (2001)), and the desire to develop artificial transcriptional activators is great (See, e.g., Ansari and Mapp, Curr. Opin. Chem. Biol. 6, 765 (2002); Mapp, Org. Biomol. Chem. 1, 2217 (2003); and Weatherman et al., Org. Biomol. Chem. 1, 3257 (2003)).

Endogenous activators contain two key functional domains: a DNA binding domain (DBD) that interacts sequence-specifically with DNA and an activation domain (AD) that mediates a variety of protein-protein interactions that lead to specific levels of gene activation (See, e.g., Ptashne and Gann, Genes & Signals; Cold Spring Harbor Laboratory: New York (2001)). These domains are exchangeable, and artificial activators that target novel DNA binding sites have successfully been generated by replacing endogenous DBDs with non-natural equivalents (See, e.g., Ansari and Mapp, Curr. Opin. Chem. Biol. 6, 765 (2002); Mapp, Org. Biomol. Chem. 1, 2217 (2003); and Weatherman et al., Org. Biomol. Chem. 1, 3257 (2003)). In contrast, it has proven a far greater challenge to replace the activation domain with a small molecule counterpart.

I. Small Molecule Activation Domains and Methods of Making the Same

Accordingly, the present invention provides novel small molecule activation domains. In some embodiments, the present invention provides activation domains comprising isoxazolidines. In some embodiments, the isoxazolidine further comprises a functional group (See, e.g., Examples 2-4, FIG. 5a). Isoxazolidines comprise a conformationally constrained, heterocyclic scaffold to which functional groups can be incorporated in a stereo-controlled manner. The present invention is not limited by the nature of the heterocyclic scaffold to which the functional groups are attached. Indeed, any conformationally constrained scaffold to which functional groups can be incorporated in a stereo-controlled manner is contemplated in the present invention (e.g., other five member scaffolds or six member rings). In some embodiments, the activation domains are synthesized as oligomers (e.g., as dimers, trimers, tetramers, etc.). In some embodiments, the activation domains are attached via linkers.

In preferred embodiments, the functional groups comprise a polar group. In some embodiments, the polar groups comprise hydroxyl groups and/or carboxylic acid groups. In preferred embodiments, the functional groups comprise a hydrophobic group. In some embodiments, the hydrophobic group comprises a phenyl group and/or an isobutyl group. In some embodiments, the functional groups are located at the N2, C3 or C5 position of the isoxazolidine and displayed in a three-dimensional array. The present invention is not limited by the nature of the functional group. Indeed any polar or hydrophobic functional group is contemplated. In a preferred embodiment of the present invention, the activation domains possess a net hydrophobic nature (See, e.g., Example 3, isoxazolidine 4).

In some embodiments, the activation domains are synthesized as described (See, e.g., Example 2, FIGS. 1-4). The present invention is not limited by any particular method or scheme of synthesis. Indeed, a variety of methods and schemes are contemplated. For example, transcriptional activation domains of the present invention may be prepared by any available methods including: recombinant nucleic acid methodologies (See, e.g., Sambrook et al., Molecular Cloning: a Laboratory Manual, 2nd Ed., Cold Spring Harbor Press, Cold Spring Harbor, N.Y. (1989); Innis et al., PCR Protocols: A Guide to Methods and Applications, Academic Press, San Diego, Calif. (1990); Erlich et al., PCR Technology: Principles and Applications for DNA Amplification, Stockton Press, New York N.Y. (1989), each of which is incorporated herein by reference), synthetic chemistry (See, e.g., Bodansky et al., The Practice of Peptide Synthesis, Springer-Verlag, New York, N.Y. (1984); Atherton et al., Solid Phase Peptide Synthesis: a Practical Approach, IRL Press at Oxford University, England (1989), each of which is incorporated herein by reference), or other techniques capable of linking the desired functional groups to a heterocyclic, conformationally constrained scaffold.

II. Methods for Screening Small Molecule/compound Libraries

The two-hybrid assay has proven to be an outstanding tool for detecting and/or characterizing protein-protein interactions. In the two-hybrid assay, one protein partner is fused to a DNA binding domain while the other potential interaction partner (or a library of potential interaction partners) is attached to a transcriptional activation domain. If the two proteins interact, a transcriptional activator is formed that drives the expression of a reporter gene (e.g., β-galactosidase) enabling ready detection of protein-protein interactions.

Two-hybrid protein-protein interaction systems have been used to identify interaction partners for known proteins by fusing the known protein to either the DNA binding domain or the transcriptional activation domain and introducing the resulting fusion into cells along with a library fused to the other of the activation domain and the DNA binding domain. Typically, such assays are performed in yeast systems, with β-galactosidase or a selectable marker (or both) as the reporter gene, but analogous systems have been developed in other cell types (See, e.g., Vasavada et al., Proc. Natl. Acad. Sci. USA 88, 10686 (1991); Fearon et al., Proc. Natl. Acad. Sci. USA 89, 7958 (1992); Finkel et al., J. Biol. Chem. 268, 5 (1993), each of which is incorporated herein by reference).

Many interacting protein pairs have been identified through the application of such systems (For reviews, see Fields et al., Trends Genet. 10, 286 (1994); Allen et al., Trends Biol. Sci. 20, 511 (1995), each of which is incorporated herein by reference), and standardized protocols can be found in readily available textbooks (See, e.g., Shirley et al., Methods Cell Biol. 49, 401 (1995), incorporated herein by reference).

To date, an analogous assay to identify small molecule-protein interactions (i.e., for the discovery of small molecule/compound ligands for specific proteins) is not available. Specifically not available is a two-hybrid-like assay in which a protein is fused to a DNA binding domain while a small molecule library/compound library is fused to an activation domain. If the small molecule/compound interacts with the protein of interest, a transcriptional activator is formed that drives the expression of a reporter gene (e.g., β-galactosidase) enabling ready detection of small molecule/compound-protein interactions. Such an assay would be an enormously powerful tool for rapidly identifying ligands for specific proteins in the context of the cell, important for pharmaceutical applications as well as for basic research. With a small molecule activation domain of the present invention, the creation of such an assay can now be utilized (See, e.g., Example 6, FIG. 12).

Accordingly, the present invention provides a method of screening a small molecule/compound library to identify ligands of a protein of interest comprising, for example, providing the protein of interest fused to a DNA binding domain, a small molecule activation domain coupled to a compound library comprising a plurality of compounds, and host cells containing a reporter gene; combining the protein of interest, the small molecule activation domain coupled to the compound library, and the host cells under conditions such that the protein of interest is able to interact with the plurality of compounds; detecting the interaction under conditions such that the activation of the reporter gene is measured; and determining the identification of the ligand. In some embodiments, the compound library comprises less than about 10,000 putative ligands. In some embodiments, the compound library comprises about 5 to about 100 putative ligands. In some embodiments the host cells are bacterial, yeast or mammalian cells.

The present invention is not limited by the nature of the small molecule/compound library. Indeed, a variety of small molecule/compound ligands are contemplated including, but not limited to, carbohydrates, monosaccharides, oligosaccharides, polysaccharides, amino acids, peptides, oligopeptides, polypeptides, proteins, nucleosides, nucleotides, oligonucleotides, polynucleotides, lipids, retinoids, steroids, glycopeptides, glycoproteins and proteoglycans. In preferred embodiments, the small molecule/compound library comprises ligands selected from the group consisting of synthetic small molecule organic compounds.

In some embodiments, a protein of interest is fused to a DNA binding domain, analogous to the original two-hybrid assay. Attached to the small molecule transcriptional activation domain (See, e.g., FIGS. 1 and 5a) is a combinatorial library of small molecules/compounds. If one of the members of the combinatorial library is a ligand for the protein of interest, a transcriptional activator is reconstituted and the reporter gene is turned on. In some embodiments, the assay is carried out in bacteria, yeast or mammalian cells with a variety of reporter genes. In preferred embodiments, the compounds that bind to the protein of interest, as determined by reporter gene expression, are identified.

The present invention is not limited by the nature of the DNA binding domain. The DNA binding domain can be any DNA binding moiety that recognizes a known DNA sequence, but preferably corresponds to or includes a DNA binding domain of a known protein, most preferably of a transcriptional regulator (See, e.g., Nelson, Curr. Op. Genet. Dev. 5, 180 (1995)). For example, the DNA binding domains used in the identification of small molecule/compound ligands for a protein of interest might be Gal4, Gal11, or LexA DNA binding domains.

Similarly, the present invention is not limited by the nature of the reporter gene utilized and can be any gene whose expression is readily detectable. For example, in yeast systems, reporters may include, but are not limited to, the β-galactosidase gene and selectable genes such as HIS3, LEU2, or URA3. In human systems, the reporter gene may be selected from the group comprising, but not limited to, those for SV40 large T antigen used in CV-1 cells (See, e.g., Vasvada et al., Proc. Natl. Acad. Sci. USA 88, 10686 (1991)); CD4, cell-surface molecules that can be selected in a cell sorter, or drug-selectable markers (See, e.g., Fearon et al., Proc. Natl. Acad. Sci. USA 89, 7958 (1992)).

Applications of the small molecule/compound library screening methods of the present invention are, of course, not limited to the identification of new small molecule/compound-protein interactions. As is well known in the art for standard two-hybrid methods, such assays can usefully be employed to test the existence or dissect the specifics of a protein-protein interaction (See, e.g., Fields et al., Trends Genet. 10, 286 (1994); Allen et al., Trends Bioch. Sci. 20, 511

(1995)) and similar methods for small molecule/compound-protein interactions are contemplated herein. For example, the significance of mutations, deletions, or insertions in different regions of the protein of interest or small molecules/compounds can be assayed by studying their effects on transcriptional activation in these systems. Techniques for producing such mutations, deletions, and insertions are well known in the art.

One of ordinary skill in the art will readily appreciate that screening for small molecule/compound ligands is not limited to a particular system or cell type. For example, assays or screens may occur in yeast, bacteria, or mammalian cells. Screens may readily be executed in systems (e.g., in mammalian cells, preferably human cells), by selecting reporter constructs that are expressed in the desired cell type, and inserting the hybrid gene library into an appropriate expression vector (that is, into a vector that directs protein in the desired cell type) Suitable expression vectors and reporter genes for a wide array of systems are well known in the art.

III. Method of Regulating Gene Expression

There are a number of small molecules currently in use for inducing the expression of specific genes (e.g., tetracycline and IPTG). These systems provide a rapid, "all on" response useful for protein over-expression as well as for turning specific genes on to study the function or role of the gene product. The disadvantage of these systems is that a specific exogenous promoter must be incorporated into the system to control the expression of the targeted gene. The small molecule transcriptional activators of the present invention offer a powerful alternative to this technology.

Accordingly, in some embodiments, the present invention provides a method of regulating expression of a gene of interest comprising providing host cells; and a small molecule activation domain fused to a DNA binding domain, and delivering to the host cells an effective amount of the small molecule activation domain fused to a DNA binding domain such that expression of the gene of interest is modified (See, e.g., Example 7). In some embodiments, the expression of the gene is induced. In some embodiments, the expression of the gene is suppressed.

When coupled to a DNA binding domain that targets a specific endogenous promoter, the small molecule activators can simply be added to the culture media to rapidly alter expression of a targeted gene or set of genes. An additional advantage of the system is that the levels of gene activation can be fine-tuned by choosing one of several different small molecule transcriptional activation domains. For example, in some embodiments, the activation domain chosen is a strong activator and induces large amounts of gene expression (See, e.g., Example 3, FIG. 5c, isoxazolidine 4). In other embodiments, the activation domain chosen is not as strong an activator and induces less gene expression (See, e.g., Example 3, FIG. 5c, isoxazolidines 2, 3, or 6).

The activation domains of the present invention can be fused to any available DNA binding moiety to create a transcriptional activator of the present invention. For example, the activation domains can be linked to a DNA-binding polypeptide (e.g., an intact protein that does not function as a transcriptional activator but binds to DNA, or any portion of a DNA-binding protein that retains DNA-binding activity) (See, e.g., Nelson, Curr. Op. Genet. Dev. 5, 180 (1995)), a DNA-binding peptide derivative (See, e.g., Wade et al., JACS 114, 8784 (1992); Mrksich et al., Proc. Natl. Acad. Sci. USA 89, 7586 (1992); Mrksich et al., JACS 115, 2572 (1993); Mrksich et al., JACS 116, 7983 (1994)), an anti-DNA antibody (See, e.g., Stollar, Faseb J., 8, 337 (1994)), a DNA intercalation compound (e.g., p-carboxy methidium, p-carboxy ethidium, acridine and elipticine), a groove binder (e.g., netropsimm, distamycin, and actinomycin, See, e.g., Waring et al., J. Mol. Recog. 7, 109 (1994)), or a nucleic acid capable of hybridizing, to form a duplex or a triplex, with a target DNA sequence (See, e.g., Gee et al., Am. J. Med. Sci. 304, 366 (1992)). In a preferred embodiment, the activation domains are linked to a sequence-specific DNA-binding moiety, so that they can be targeted to a selected DNA site from which to activate transcription.

Any available linkage (e.g., covalent bonding, hydrogen bonding, hydrophobic association, etc.) may be utilized to associate the activation domain to a DNA binding moiety, so long as the DNA-binding activity of the DNA-binding moiety and the transcriptional activation activity of the activation domain are preserved. The linkage between the activation domain and the DNA binding domain may be direct or may alternatively may be mediated by a linker or a "linkage factor". A linkage factor is any entity capable of mediating a specific association between the DNA binding moiety and the activation domain while preserving the activities of both. The term "specific association" has its usual meaning in the art: an association that occurs even in the presence of competing non-specific associations. The concept of linkage factors is known in the field of transcriptional activation and its scope and significance will readily be appreciated by those of ordinary skill in the art. For example, rapamycin can act as a linkage factor when it mediates interactions between a DNA binding moiety that includes, for example, FK506 binding protein and a transcriptional activating moiety that includes a cyclophilin (See, e.g., Belshaw et al., Proc. Natl. Acad. Sci. USA 93, 4604 (1996)).

Preferred transcriptional activators of the present invention comprise a substantially hydrophobic, small molecule activation domain, described above, linked to a DNA-binding polypeptide that preferably has sequence-specific DNA binding activity. In particularly preferred embodiments, the activation domain is linked to the DNA binding domain (e.g., a sufficient portion of the protein to recognize DNA but not to have transcriptional regulatory activity in the absence of the attached activation domain) of a transcriptional regulatory protein (See, e.g., Klug, Ann. NY Acad. Sci. 758, 143 (1995)). The choice of DNA binding domain will of course depend on the gene intended to be activated. In preferred embodiments, the DNA binding domain recognizes a site positioned relative to the transcriptional start site of the gene such that the activation domain can affect transcription. In some embodiments, the DNA binding domain binding site is within approximately 250-1000 base pairs of the transcription start site. In some embodiments, (e.g., in higher mammalian systems, e.g., human), transcriptional activators are known to be effective when bound several thousand basepairs away (upstream or downstream) of the transcription start site (See, e.g., Serneza, Hum. Mutat. 3, 180 (1994); Hill et al., Cell 80, 199 (1995)).

One of ordinary skill in the art will readily appreciate that regulation of gene expression is possible in multiple systems and cells. For example, regulating gene expression by the methods described above may occur in yeast, bacteria or mammalian cells. In a preferred embodiment, the regulation of gene expression occurs in human cells.

The novel activation domains described herein are particularly useful for introduction into cells to stimulate transcription therein since these new activation domains, even when over-expressed, do not interfere with transcriptional activation by classical activators such as the acidic activators. These activators are therefore highly useful for all applications involving controlled gene activation.

The novel activation domains of the present invention can be delivered to cells by any of a variety of available techniques. For example, when coupled to a DNA binding domain that targets a specific endogenous promoter, the small molecule activation domains can simply be added to the culture media to rapidly induce expression of a targeted gene or set of genes. Alternatively, the activation domains may be delivered by means of known drug delivery systems such as lipid micelles, or any other available technique.

IV. Transcription Based Therapeutics and Research Applications

A growing number of human diseases, ranging from cancer to metabolic disorders, are characterized by aberrant transcription patterns and malfunctioning transcriptional regulators are often at the heart of these disease states. For example, diabetes results from reduced expression of insulin, and many cancers are caused by mutation of tumor-suppressor genes. One of the better studied examples is acute promyelotic leukemia (APL), the origin of which is a block in hemopoietic development of myeloid cells at the promylelocytic stage. This block is linked to chromosomal translocations that produce chimeric versions of the transcriptional activator retinoic acid receptor-α (RARα). Through interactions with histone deacetylases, the chimeric RARα proteins repress a number of genes necessary for normal growth. Although treatment of APL with large doses of retinoic acid can induce remission, relapse and resistance to retinoic acid remains a substantial therapeutic challenge. Hence, artificial transcriptional activators that can specifically upregulate APL-associated genes to desired levels have a large therapeutic role.

Current approaches are severely limited by the necessity of using peptide-based transcriptional activation domains in the construction of artificial activators as they suffer from proteolytic instability and poor cellular permeability. Synthetic small molecule activation domains that replicate endogenous transcriptional activation domain function in the cell permits transcription-based therapeutics for the treatment of human diseases such as APL.

Accordingly, the present invention provides methods for regulating expression of a gene of interest in a subject, for the purpose of analyzing the effect of the compounds, modulating transcription to assist with therapy (e.g., co-administered with existing therapies) or as a stand alone therapy, comprising: providing a subject and a small molecule activation domain linked to a DNA binding domain and delivering to the subject an effective amount of the small molecule activation domain such that expression of the gene of interest is modified (See, e.g., Example 8). Hence, in some embodiments, the activation domains of the present invention can be employed to treat or analyze the above mentioned class of diseases. Specifically, an activation domain of the present invention is linked to a DNA binding domain that recognizes a site appropriately located relative to the relevant gene so that the activator is effective when bound to the site. The activator is then delivered to appropriate cells by any available technique and is allowed to stimulate gene transcription.

The present invention therefore encompasses methods of activating transcription by providing a novel activation domain to a cell and recruiting that activation domain to a promoter where it activates transcription. In preferred embodiments of the invention, the activation domain is recruited to the DNA by virtue of its being covalently attached to a DNA binding domain.

V. Other Embodiments

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

For example, as mentioned above, all of the assays described herein can be performed in any of a variety of cell types. Yeast cells are often selected as the most convenient for experimental manipulation, but even there, the variety of yeast strains that are available affords a wide range of opportunity for the practice of the present invention. Bacterial and mammalian (e.g., human cells) cells serve as other cells in which the present invention is applicable.

EXPERIMENTAL

The following examples are provided in order to demonstrate and further illustrate certain preferred embodiments and aspects of the present invention and are not to be construed as limiting the scope thereof.

In the experimental disclosure that follows, the following abbreviations apply: ° C. (degrees Centigrade); cm (centimeters); g (grams); l or L (liters); µg (micrograms); µl (microliters); µm (micrometers); µM (micromolar); µmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); bp (base pairs); Promega (Promega Corporation, Madison, Wis.); New England Biolabs (New England Biolabs, Beverly, Mass.); Invitrogen (Invitrogen Corp., Carlsbad, Calif.); Biosearch Technologies (Biosearch Technologies, Novato, Calif.); Fisher (Fisher Scientific, Pittsburgh, Pa.); Millipore (Millipore, Billerica, Mass.); Qiagen (Qiagen, Santa Clarita, Calif.); Bio-Rad (Bio-Rad Laboratories, Hercules, Calif.); 1 (2-{4-((2,4-diamino-pteridin-6-ylmethyl)-methyl-amino)-benzoylamino}-4-hydrazinocarbonyl-(S)-butyric acid); 2 (4-((3RS, 5RS)-3-Allyl-2-benzyl-3-isobutyl-isoxazolidin-5-yl-methylenehydrazinocarbonyl)-2-(4({(6-(amino-methylcarbaminidoylimino-methyl)-pyrazin-2-ylmethyl)-methyl-amino}-methyl)-benzoylamino)-(S)-butyric acid); 3 (2-(4({(6-(Amino-methylcarbaminidoylimino-methyl)-pyrazin-2-ylmethyl)-methylamino}-methyl)-benzoylamino)-4-{2-((5RS)-hydroxymethyl-2-(hydroxy-2-oxopropyl)-(3RS)-isobutyl-isoxazolidin-3-yl)-ethylidene-hydrazinocarbonyl}-(S)-butyric acid); 4 (2-(4({(6-(Amino-methylcarbaminidoylimino-methyl)-pyrazin-2-ylmethyl)-methylamino}-methyl)-benzoylamino)-4-(2-benzyl-(3RS)-(2-hydroxy-ethyl)-3-isobutylisoxazolidin-(5RS)-ylmethylene-hydrazinocarbonyl)-(S)-butyric acid); 5 (2-(4({(6-(Amino-methylcarbaminidoylimino-methyl)-pyrazin-2-ylmethyl)-methylamino}-methyl)-benzoylamino)-4-(2-benzyl-(3RS)-(3-hydroxy-2-methoxy-propyl)-(3RS)-isobutyl-isoxazolidin-(5RS)-ylmethylene-hydrazinocarbonyl)-(S)-butyric acid); 6 (2-(4({(6-(Amino-methylcarbaminidoylimino-methyl)-pyrazin-2-ylmethyl)-methylamino}-methyl)-benzoylamino)-4-(2-(2-benzyl-(5RS)-hydroxymethyl-(3RS)-isobutylisoxazolidin-3-yl)-ethylidene-hydrazinocarbonyl)-(S)-butyric acid); 8 ((3-Isobutyl-4,5-dihydro-isoxazol-5-yl)-methanol), unless indicated otherwise herein.

EXAMPLE 1

Materials and Methods

General molecular biology methods. HeLa nuclear extracts, nucleotide triphosphates, and $MgCl_2$ were purchased from Promega and used in accordance with manufacturer instructions. Restriction endonucleases and T4 DNA Ligase were purchased from New England Biolabs and used as directed. Oligonucleotides, DH5α E: coli, and BL21(DE3) pLysE E. coli used for plasmid construction, amplification, and protein expression were obtained from Invitrogen. Molecular beacons were purchased from Biosearch Technologies. The plasmid encoding LexA-eDHFR (pWA02) has been described (See, e.g., Baker et al., Anal. Biol. 315 134 (2003)). All other chemicals and supplies were purchased from Fisher unless otherwise noted. All other molecular biology techniques were carried out as described (See, e.g., Sambrook et al., Molecular Cloning, a Laboratory Manual; 2nd ed; Cold Spring Harbor Press: Plainview (1989)).

Template construction. The DNA template for in vitro transcription was constructed from a pUC18 plasmid. The molecular beacon complement was placed 150 bp downstream of the TATA box to assure transcription elongation was observed and aborted transcripts would not be visualized and two tandem LexA binding sites were placed 75 bp upstream of the TATA box. First, the AdML promoter was inserted into the plasmid by annealing the oligonucleotides (5'-AGC TTT GAG GAC GAA CGC GCC CCC ACC CCC TTT TAT AGC CCC CCT TCA GGA ACA CCT GAG CCG ATT GCT GGC GAT CAA CGC GTA AAG CCG ATA GCC GAC-3' (SEQ ID NO:1)) and (5'-CTA GGT CGG CTA TCG GCT TTA CGC GTT GAT CGC CAG CAA TCG GCT CAG GTG TTC CTG AAG GGG GGC TAT AAA AGG GGG TGG GGG CGC GTT CGT CCT CAA-3' (SEQ ID NO:2)) producing sticky ends that could be cloned into pUC18 following its digestion with HindIII/XbaI (See, e.g., Aso et al., J. Biol. Chem. 42, 26575 (1994)). Next the LexA binding sites were inserted 60 base pairs from the TATA box by annealing (5'-GATCCA CTG CTG TAT ATA AAA CCA GTG GTT ATA TGT ACA GTA GAC TGC TGT ATA TAA AAC CAG TGG TTA TAT GTA CAG TAG AGA TCT T-3' (SEQ ID NO:3)) and (5'-AAT TAA GAT TCC TAC TGT ACA TAT AAC CAC TGG TTT TAT ATA CAG CAG TCT ACT GTA CAT ATA ACC ACT GTT TTT ATA TAC AGC AGT G-3' (SEQ ID NO:4)) producing sticky ends that could be cloned into the AdML containing pUC18 plasmid following its digestion with BamHI and EcoRI (See, e.g., Dumoulin et al., Biochemistry 35, 4279 (1996)). Lastly, the molecular beacon compliment was inserted by annealing (5'-TAT GAA AAA AAG TTA AGA CCT ATG CTC GCT-3' (SEQ ID NO:5)) and (5' GCG CAG CGA GCA TAG GTC TTA ACT TTT TTT CA-3' (SEQ ID NO:6)) producing sticky ends that could be inserted into the LexA and AdML containing plasmid following its digestion with KasI/NdeI. All intermediate and final plasmids were amplified in DH5α E. coli, selected on LB-agar plates containing 0.1 mg/mL ampicillin, and isolated from cultures using a QIAprep Spin Miniprep Kit (Qiagen). The sequences of the isolated plasmids were verified by sequencing.

LexA-eDHFR expression and purification. The LexA-eDHFR plasmid pWA02 was transformed into chemically competent BL21(DE3) pLysE E. coli (Invitrogen) and cells were plated onto LB-agar plates supplemented with ampicillin (0.1 mg/mL) and chloramphenicol (0.034 mg/mL). Cultures (50 mL) from single colonies were grown overnight at 37° C. (275 rpm) in LB supplemented with ampicillin (0.1 mg/mL) and chloramphenicol (0.034 mg/mL) before addition to 1 L of LB supplemented with ampicillin (0.1 mg/mL). After 3 h, the cultures were cooled to 16° C., and expression was induced with IPTG (final concentration 0.5 mM) for 5 h. Cells were harvested through centrifugation at 4° C. and 5000 RPM for 20 minutes. The cell pellet was resuspended in lysis buffer (50 mM NaH2PO4 (pH 8.0), 300 mM NaCl, 10 mM imidazole, 10 mM β-mercaptoethanol, and 10% glycerol), lysed using sonication, and the His tagged protein was isolated from the cell lysate using Ni2+ charged agarose beads (Qiagen). The resinbound protein was then washed with lysis buffer supplemented with 20 mM imidazole and eluted with lysis buffer supplemented with 250 mM imidazole. Storage buffer (40 mM Tris (pH 7.8), 100 mM KCl, 0.2 mM EDTA, 0.5 mM PMSF, 0.5 mM DTT, and 25% glycerol) was then exchanged with the lysis buffer with the use of an Amicon® Ultra-4 centrifugal filter unit with a NMWL of 5,000 Da (Millipore). Lastly, the protein was snap frozen and stored at −78° C. in storage buffer. Protein purity was determined through SDS-PAGE and protein concentration was measured using Bradford reagent (BioRad).

In vitro transcription. The in vitro transcription reactions were monitored with molecular beacons and accomplished using standard protocols (See, e.g., Marras et al., Nucleic Acids Res. 32, e72 (2004); Liu et al., Anal. Biochem. 300, 42 (2002); Lue et al., Methods Enzymol. 194, 545 (1991); Lue et al., Science 246, 661 (1989); Lee and Roeder Mol. Cell. Biol. 1, 635 (1981)). For each reaction, 100 ng of template DNA was incubated with 50 nM LexA-eDHFR and 50 nM activator or negative control in a buffer containing 5 mM MgCl2, 400 mM of each NTP, 10 µg of salmon sperm carrier DNA, 10 mM HEPES (pH 7.9), 50 mM KCl, 0.1 mM EDTA, 0.25 mM DTT, and 10% glycerol in 50 mL at 30° C. All reactions were initiated by the addition of 8 units of HeLa nuclear extracts and were incubated at 30° C. for 60 min. Following the 60 min incubation, the reaction was terminated by the addition of NaCl at a final concentration of 500 mM. Molecular beacon was added in simultaneously at a concentration of 100 nM. Fluorescence signal was measured on a SpexFluoromax-2 with excitation and emission wavelengths at 492 nm and 520 nm respectively. An internal standard consisting of a mismatch molecular beacon with a Quasar 670 fluorophore ($\lambda_{ex}$=649, $\lambda_{em}$=670) was also added to each reaction. Fluorescence intensity at 520 nm was divided by intensity at 670 nm to give a normalized intensity. To obtain fold activation, each individual experiment was divided by the average of two control reactions containing compound 1. For FIG. 5C, the fold activities were converted to percent activation relative to the activity of ATF14.

EXAMPLE 2

Synthesis of Activation Domains

General synthesis strategies. The isoxazolidine-methotrexate conjugates were synthesized using one of two routes (See, e.g., FIG. 1). The key point of divergence in the two routes is in the position of methotrexate attachment. For conjugates 2, 4, and 5, the C5 hydroxymethyl substituent was oxidized to an aldehyde, and this was used for hydrazone formation with compound 1. For conjugates 3 and 6, the hydrazone linkage with 1 was formed after oxidation of the C3 allyl substituent to an aldehyde as outlined below (See, e.g., FIGS. 2-4).

General synthetic methods. Unless otherwise noted, starting materials were obtained from commercial suppliers and used without further purification. CH2Cl2, CH3CN and THF were dried by passage through activated alumina columns and degassed by stirring under a dry N2 atmosphere (See, e.g., Pangborn et al., Organometallics, 15, 1518 (1996)). All reactions were performed under a dry N2 atmosphere unless otherwise specified. BF3.OEt2 and Et3N were distilled from CaH2. MeOH was distilled from sodium metal. Purification by flash chromatography was carried out with E. Merck Silica Gel 60 (230-400 mesh) according to known procedures (See, e.g., Still et al., J. Org. Chem. 43, 2923(1978)). $^1$H and $^{13}$C NMR spectra to measure purity were recorded in CDCl3 at 500 MHz and 125 MHz, respectively, unless otherwise specified (See, e.g., FIG. 11). IR spectra were measured as thin films on NaCl plates. Reverse-phase HPLC purification performed on a Varian ProStar 210 equipped with Rainin Dynamax UV-D II detector using a C 18 (8×100 mm) Radial-Pak™ cartridge in 20 mM NH4OAc/MeOH measured at λ=254 nm unless otherwise specified. UV-vis spectra were measured in MeOH. Normal-phase HPLC purification was performed on Varian ProStar 210 equipped with Varian ProStar UV-VIS 345 detector using a SiO2 (25×100 mm) Radial-Pak™ cartridge in hexanes/EtOAc. In order to determine the concentration of all methotrexate conjugates (2-6 and ATF14 coupled to methotrexate), the characteristic UV-vis absorption of methotrexate at λ max=257, 302, and 370 nm with extinction coefficients of 23,000, 22,000, and 7,100 M-1 cm-1 was used (See, e.g., Seeger, et al., J. Am. Chem. Soc. 71, 1753 (1949)). Once the concentration was determined, the sample was aliquoted, lyophilized, and stored at –78° C. Before an experiment was carried out, the sample was reconstituted in buffer (10 mM HEPES (pH 7.9), 50 mM KCl, 0.1 mM EDTA, 0.25 mM DTT, and 10% glycerol) and the concentration was again determined. Full fluorescence spectra were run on all methotrexate conjugates to insure no spectral overlap with the molecular beacon fluorophores.

(3-Isobutyl-4,5-dihydro-isoxazol-5-yl)-methanol (8)

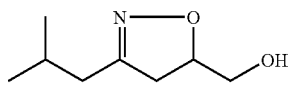

8

Compound 8 was prepared according to literature procedures (See, e.g., Bode et al., Angew. Chem., Int. Ed. 40, 2082 (2001)). Purification by Kugelrohr distillation (160° C. @0.05 mmHg) provided 3.67 g of isoxazoline 8 in 78% yield as colorless oil. IR: 3391, 2955, 1464, 1368, 1048 cm$^{-1}$; $^1$H NMR: d 0.93 (d, 3H, J=5.4), 0.94 (d, 3H, J=5.4), 1.86-1.92 (m, 2H), 2.19-2.21 (m, 2H), 2.80 (dd, 1H, J=16.8, 7.3), 2.93 (dd, 1H, J=17.1, 10.7), 3.54 (dd, 1H, J=12.2, 4.6), 3.75 (dd, 1H, J=11.9, 2.9), 4.62-4.68 (m, 1H); $^{13}$C NMR: δ 22.21, 22.36, 26.07, 36.37, 38.56, 63.62, 79.73, 158.93; HRMS (EI) calcd for $(C_8H_{15}NO_2)$+:157.1103, found: 157.1096.

(3-Allyl-3-isobutyl-isoxazolidin-5-yl)-methanol (S1)

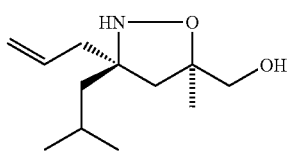

S1

S1 was prepared according to literature procedures (See, e.g., Minter et al., J. Am. Chem. Soc. 125, 6846 (2003)) to give 2.29 g of isoxazolidine S1 in 92% yield as a colorless oil after passage through a short plug of SiO$_2$ to remove baseline impurities. A diastereomeric ratio of 6:1 was determined by 1H NMR spectral integration of the crude mixture with the major diastereomer assignment shown based on 1H NMR shift comparison to known compounds (See, e.g., Minter et al., J. Am. Chem. Soc. 125, 6846 (2003)). The minor diastereomer was removed at a later stage (vide infra). IR: 3209, 2952, 1450, 1039, 909 cm$^{-1}$; $^1$H NMR (major diastereomer only): d 0.92 (d, 3H, J=6.6), 0.94 (d, 3H, J=6.8), 1.38 (dd, 1H, J=14.2, 6.3), 1.44 (dd, 1H, J=14.2, 6.3), 1.62 (dd, 1H, J=12.2, 7.3), 1.77-1.84 (m, 1H), 2.19-2.24 (m, 2H), 2.36 (dd, 1H, J=14.2, 6.8), 3.53 (dd, 1H, J=12.0, 5.9), 3.69 (dd, 1H, J=12.2, 2.9), 4.17-4.21 (m, 1H), 5.08-5.12 (m, 2H), 5.79-5.87 (m, 1H); $^{13}$C NMR (major diastereomer only): δ 23.83, 24.11, 39.87, 41.73, 44.24, 44.80, 63.60, 67.19, 81.40, 117.99, 134.33; HRMS (ESI) calcd for $(C_{11}H_{21}NO_2+Na)$+: 222.1470, found: 222.1466.

Procedure for the N-alkylation of S2: To a solution of isoxazolidine S1 (2.29 g, 11.49 mmol, 1 eq) in THF (109 mL) were added DMAP (0.07 g, 0.58 mmol, 0.05 eq), Et3N (2.24 mL, 16.09 mmol, 1.4 eq), and TBSOTf (3.70 mL, 16.09 mmol, 1.4 eq) to protect the primary alcohol in 97% yield following purification by flash chromatography (9:1 hexanes/EtOAc). To a solution of TBS-protected isoxazolidine S2 (0.17 g, 0.53 mmol, 1 eq) in DMF (2 mL) was added i-Pr2NEt (0.28 mL, 1.59 mmol, 3 eq) and BnBr or tert-butylbromoacetate (2.64 mmol, 5 eq). The reaction mixture was irradiated in a 1000 W microwave (5×15 s) @ 30% power with mixing between each interval. Once the reaction was complete by TLC analysis, the reaction was diluted with H$_2$O (15 mL), and extracted with Et$_2$O (3×15 mL). The combined organic extracts were washed with H$_2$O (1×20 mL), brine (1×20 mL), dried over Na$_2$SO$_4$, filtered, and concentrated in vacuo.

3-Allyl-2-benzyl-5-(tert-butyl-dimethyl-silanyloxymethyl)-3-isobutyl-isoxazolidine (S3)

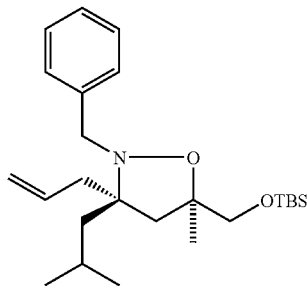

S3

Purification by flash chromatography (98:2 hexanes/EtOAc) provided isoxazolidine S3 as a colorless oil (the major diastereomer was isolated by normal-phase HPLC for characterization purposes and for the synthesis of 2). IR: 2952, 2855, 1454, 1360, 1253, 1119, 835 cm$^{-1}$; $^1$H NMR: δ –0.04 (s, 3H), –0.02 (s, 3H), 0.84 (s, 9H), 0.94 (d, 3H, J=6.6), 0.97 (d, 3H, J=6.6), 1.32-1.35 (m, 1H), 1.59 (dd, 1H, J=14.4, 4.9), 1.83-1.89 (m, 1H), 1.90-1.96 (m, 1H), 2.21 (dd, 1H, J=12.0, 8.8), 2.25-2.34 (m, 1H), 2.35-2.44 (m, 1H), 3.48-3.58 (m, 1H), 3.67 (dd, 1H, J=10.3, 5.9), 3.78-3.85 (m, 2H), 4.00-4.10 (m, 1H), 5.04-5.16 (m, 2H), 5.88-5.96 (m, 1H), 7.18-7.40 (m, 5H); $^{13}$C NMR: δ –5.58, –5.48. 18.21, 24.06, 24.50, 25.05, 25.82, 38.80, 39.47, 43.46, 53.63, 65.47, 68.38, 76.36, 117.50, 126.57, 128.09, 128.28, 135.35, 139.30; HRMS (ESI) calcd for $(C_{24}H_{41}NO_2Si+Na)+$: 426.2804, found: 426.2798.

(3-Allyl-5-(tert-butyl-dimethyl-silanyloxymethyl)-3-isobutyl-isoxazolidin-2-yl)-acetic acid tert-butyl ester (S4)

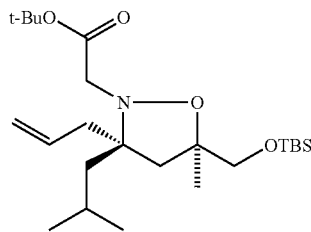

Purification by flash chromatography (95:5 hexanes/EtOAc) provided isoxazolidine S4 as a colorless oil (the major diastereomer was isolated by normal-phase HPLC for characterization purposes and for the synthesis of 3). IR: 2930, 2954, 1756, 1730, 1155 cm$^{-1}$; $^1$H NMR: δ 0.04 (s, 3H), 0.05 (s, 3H), 0.87 (s, 9H), 0.93-0.94 (d, 6H), 1.20 (dd, 1H, J=14.2, 7.1), 1.44 (s, 9H), 1.52 (dd, 1H, J=14.4, 4.9), 1.77-1.82 (m, 1H), 1.91 (dd, 1H, J=12.5, 7.3), 2.14 (dd, 1H, J=12.5, 8.1), 2.24-2.25 (m, 2H), 3.37 (m, 2H), 3.58 (dd, 1H, J=10.5, 5.4), 3.71 (dd, 1H, J=10.5, 5.1), 4.05-4.10 (m, 1H), 5.04-5.07 (m, 2H), 5.84-5.92 (m, 1H); $^{13}$C NMR: δ −5.40, −5.35, 18.29, 24.07, 24.17, 24.99, 25.91, 28.02, 39.06, 39.54, 43.07, 53.98, 65.09, 68.79, 77.40, 80.62, 117.46, 134.98, 168.93; HRMS (ESI) calcd for $(C_{23}H_{45}NO_4Si+Na)+$:450.3016, found: 450.3029.

(3-Allyl-2-benzyl-3-isobutyl-isoxazolidin-5-yl)-methanol (S5)

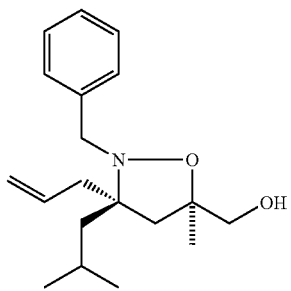

Following N-alkylation, the crude reaction was dissolved in THF to which TBAF (1.5 eq based on starting S2) was added. Following deprotection, purification by flash chromatography (7:3 hexanes/EtOAc) provided 1.72 g of N-benzyl isoxazolidine S5 in 84% yield from S2 as a mixture of diastereomers. The major diastereomer was then isolated by normal-phaseHPLC and used in subsequent steps. IR: 3394, 2952, 2863, 1450, 1028, 733 cm$^{-1}$; $^1$H NMR (400 MHz): δ 0.97 (d, 3H, J=4.8), 0.98 (d, 3H, J=4.8), 1.39 (dd, 1H, J=14.3, 6.6), 1.62 (dd, 1H, J=14.7, 4.8), 1.87-1.93 (m, 1H), 2.01-2.08 (m, 1H), 2.18-2.24 (br s, 1H), 2.28 (dd, 1H, J=12.5, 8.8), 2.45 (dd, 1H, J=13.9, 7.3), 3.53-3.61 (m, 2H), 3.83 (d, 1H, J=14.6), 3.90 (d, 1H, J=14.3), 4.02-4.10 (m, 1H), 5.09-5.13 (m, 2H), 5.88-5.99 (m,1H), 7.20-7.40 (m, 5H); $^{13}$C NMR: δ 24.10, 24.40, 25.19, 38.59, 38.71, 43.87, 53.38, 65.55, 68.47, 75.42, 117.78, 126.95, 127.91, 128.42, 135.18, 138.93; HRMS (ESI) calcd for $(C_{18}H_{27}NO_2+Na)_+$: 312.1939, found: 312.1945.

3-Allyl-2-benzyl-5-dimethoxymethyl-3-isobutyl-isoxazolidine (S6)

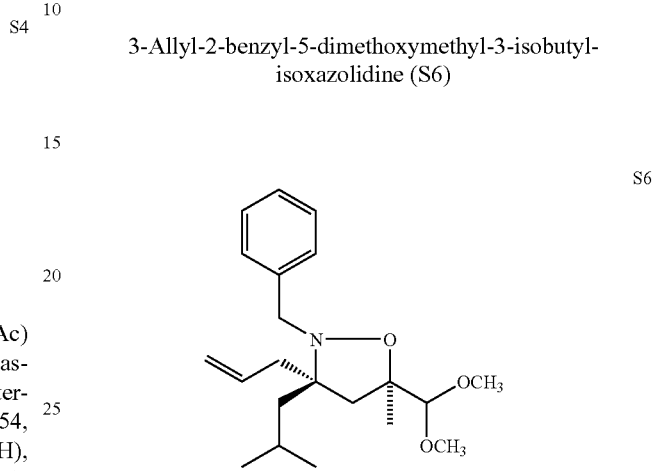

To a solution of isoxazolidine S5 (170 mg, 0.57 mmol, 1 eq) in CH$_2$Cl$_2$(6.7 mL) cooled in an ice-H$_2$O bath was added DMSO (2.44 mL, 34.4 mmol, 60 eq) and Et$_3$N (2.39 mL, 17.20 mmol, 30 eq) followed by SO$_3$.pyr (1.09 g, 6.88 mmol, 12 eq). The reaction mixture was allowed to stir with continued cooling until complete by TLC analysis (1 h). The reaction was then diluted with a 1:1 mixture of sat. NH$_4$Cl/H$_2$O (75 mL) and extracted with CH$_2$Cl$_2$ (3×25 mL). The combined organic extracts were washed with H$_2$O (1×50 mL) and brine (1×50 mL), dried over Na$_2$SO$_4$, filtered, and concentrated in vacuo. The crude aldehyde was dissolved in MeOH (1.3 mL) to which HC(OCH$_3$)$_3$ (4.39 mL, 40.1 mmol, 70 eq based on starting alcohol) and TsOH (5 mg, 0.03 mmol, 0.05 eq based on starting alcohol) were added. The reaction mixture was allowed to stir at ambient temperature until no aldehyde remained as detected by ESI-MS (48 h). The reaction was cooled in an ice-H$_2$O bath, diluted with H$_2$O (50 mL) and extracted with Et$_2$O (3×15 mL). The combined organic extracts were washed with H$_2$O (1×50 mL) and brine (1×50 mL), dried over Na$_2$SO$_4$, filtered, and concentrated in vacuo. Purification by flash chromatography (9:1 hexanes/EtOAc) provided 118 mg of dimethoxyacetal S6 in 62% yield. IR: 2952, 2829, 1454, 1082 cm$^{-1}$; $^1$H NMR (400 MHz): δ 0.97 (d, 3H, J=5.9), 0.98 (d, 3H, J=5.9), 1.35(dd, 1H, J=14.3, 6.6), 1.60 (dd, 1H, J=14.7, 5.1), 1.85-1.91 (m, 1H), 2.09 (dd, 1H, J=12.8, 6.6), 2.23-2.29 (m, 2H), 2.40 (dd, 1H, J=13.6, 7.0), 3.24 (s, 3H), 3.35 (s, 3H), 3.83(d, 1H, J=14.7), 3.87 (d, 1H, J=14.7), 3.94 (dd, 1H, J=15.0, 6.6), 4.23 (d, 1H, J=6.6), 5.06-5.11 (m, 2H), 5.89-5.97 (m, 1H), 7.17-7.38 (m, 5H); $_{13}$C NMR: d 24.09, 24.50, 25.11, 38.72, 39.96, 43.58, 53.48, 54.86, 55.44, 68.35, 75.99, 106.06, 117.66, 126.66, 128.05, 128.31, 135.19, 139.17; HRMS (ESI) calcd for $(C_{20}H_{31}NO_3+Na)_+$: 356.2202, found: 356.2203.

2-{4-((2,4-diamino-pteridin-6-ylmethyl)-methyl-amino)-benzoylamino}-4-hydrazinocarbonyl-(S)-butyric acid (1)

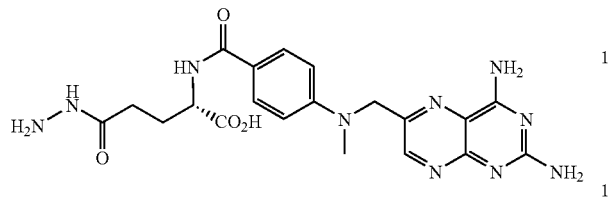

Compound 1 was prepared according to literature procedures (See, e.g., Althoff et al., Angew. Chem. Int. Ed. 41, 2327 (2002); Kralovec et al., J. Med. Chem. 32, 2426 (1989)). Reverse-phase HPLC purification using 0.1% TFA/CH3CN provided 1 as a yellow powder. UV ($\lambda_{max}$ nm): 258, 305, 372; IR: 3165, 1652, 1506, 1200 cm$^{-1}$; $^1$H NMR (CD$_3$OD): δ2.07-2.12 (m, 1H), 2.32-2.37 (m, 1H), 2.41-2.44 (m, 2H), 3.26(s, 3H), 4.60 (dd, 1H, J=9.5, 4.9), 4.92 (s, 2H), 6.86 (d, 2H, J=9.0), 7.77 (d, 2H, J=9.0),8.64 (s, 1H); $^{13}$C NMR (CD$_3$OD): ☐27.99, 30.97, 39.81, 53.41, 56.78, 112.80, 122.86, 123.56, 130.49, 147.09, 150.43, 153.15, 153.88, 157.93, 165.10, 170.38, 173.60, 175.22; HRMS (ESI) calcd for (C$_{20}$H$_{24}$N$_{10}$O$_4$+H)+: 469.2060, found: 469.2059.

Figure 9:
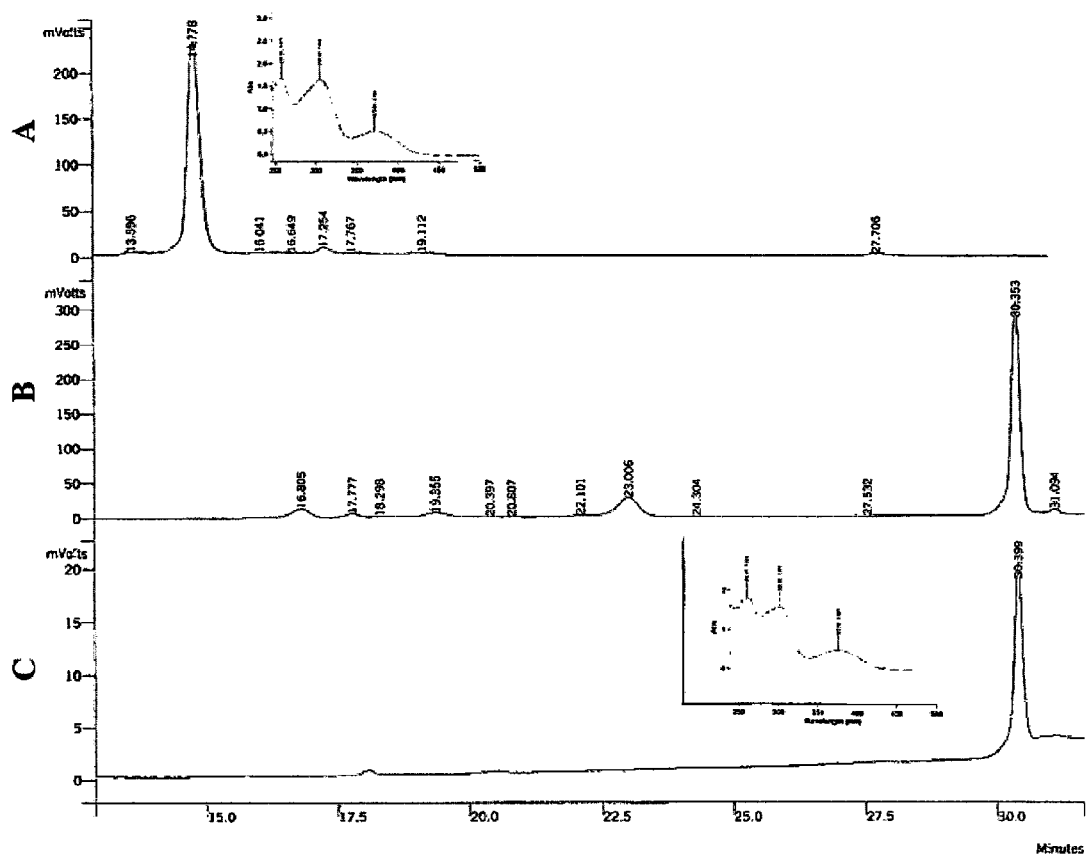
FIG. 9 depicts:
A) reverse-phase HPLC of 2-{4-((2,4-diamino-pteridin-6-ylmethyl)-methyl-amino)-benzoylamino}-4-hydrazinocarbonyl-(S)-butyric acid.

General procedure for methotrexate hydrazide/isoxazolidine condensation: To a solution of methotrexate hydrazide 1 (1-1.5 mg, 1 eq) in DMF (0.15 mL) was added isoxazolidine aldehyde (2 eq) dissolved in THF (0.15 mL). The reaction was stirred at ambient temperature, shielded from light for 24 h. The mixture was then concentrated to half-volume under high vacuum (0.05 mm Hg) and a portion was subjected to reverse phase HPLC purification (See, e.g., FIG. 9 for HPLC traces of a conjugation reaction and FIG. 10 for analytical HPLC traces and UV-vis spectra of conjugates prepared by this method).

4-((3RS, 5RS)-3-Allyl-2-benzyl-3-isobutyl-isoxazolidin-5-ylmethylene-hydrazinocarbonyl)-2-(4({(6-(amino-methylcarbaminidoylimino-methyl)-pyrazin-2-ylmethyl)-methyl-amino}-methyl)-benzoylamino)-(S)-butyric acid (2)

SO$_3$.pyridine oxidation of S5 as described for the preparation of S6 was used to generate the aldehyde that was immediately used in a conjugation reaction with 1. Reverse-phase HPLC purification provided 2 as yellow solid that was stored at −78° C., shielded from light. The purity of 2 was confirmed by analytical reverse-phase HPLC immediately after isolation and again prior to use in any in vitro transcription reactions. The identity was verified by mass spectral analysis of the isolated construct. UV ($\lambda_{max}$ nm): 258, 300, 375: HRMS (ESI) calcd for (C$_{38}$H$_{47}$N$_{11}$O$_5$+H)$_+$: 738.3840, found: 738.3840.

3-(2-Benzyl-5-dimethoxymethyl-3-isobutyl-isoxazolidin-3-yl)-propane-1,2-diol (S7)

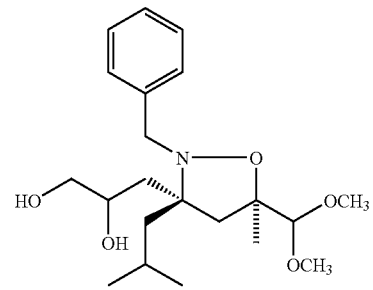

To a solution of dimethoxyacetal S6 (26 mg, 0.08 mmol, 1 eq) in t-BuOH (610 μl) and THF (160 μl) was added NMO (11 mg, 0.09 mmol, 1.2 eq) and H$_2$O (60 μl). To this solution was added OSO$_4$(80 μl of a 2.5 wt % solution in t-BuOH, 0.008 mmol, 0.1 eq). The reaction mixture was allowed to stir at ambient temperature until complete by TLC analysis (6 h). The reaction was cooled in an ice-H$_2$O bath and quenched by the addition of Na$_2$SO$_3$ (20 mg) and allowed to stir for 1 h. The mixture was then diluted with H$_2$O (10 mL) and extracted with EtOAc (3×10 mL). The combined organic extracts were dried over Na$_2$SO$_4$, filtered, and concentrated in vacuo. The crude product was obtained in quantitative yield and $^1$H NMR spectral integration revealed a 1:1 mixture of diastereomers at the newly formed 2° OH. R$_f$: 0.35 and 0.39 (2:8 hexanes/EtOAc); IR: 3359, 2951, 1455, 1067 cm$^{-1}$; $^1$H NMR (unresolved diastereomeric mixture at the 2° OH): δ 0.96-1.02 (6H), 1.30-1.50 (2H), 1.60-1.78 (3H), 1.91-2.39 (4H), 3.28-3.41 (6H), 3.43-3.63 (2H), 3.78-3.83 (1H), 3.90-4.38 (4H), 7.23-7.36 (5H); ESI-MS calcd for (C$_{20}$H$_{33}$NO$_5$+H)+: 368.2, found: 368.2.

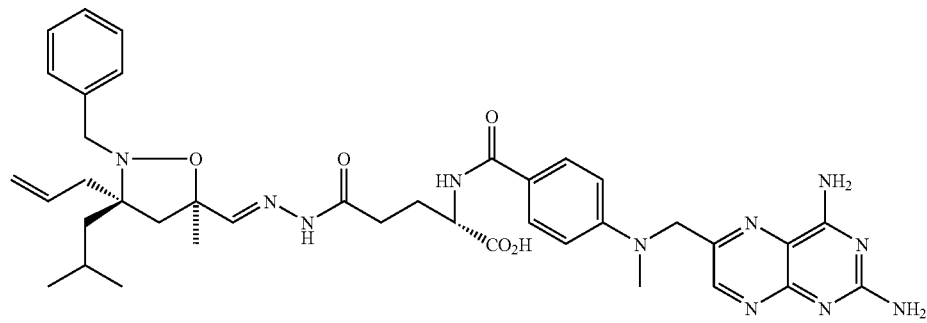

2-(4({(6-(Amino-methylcarbaminidoylimino-methyl)-pyrazin-2-ylmethyl)-methylamino}-methyl)-benzoylamino)-4-(2-benzyl-(3RS)-(3-hydroxy-2-methoxy-propyl)-(3RS)-isobutyl-isoxazolidin-(5RS)-ylmethylene-hydrazinocarbonyl)-(S)-butyric acid (5)

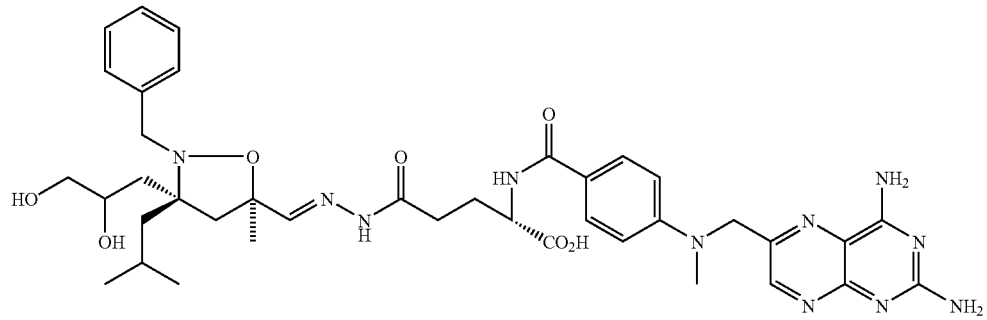

A solution of diol S7 (13 mg, 0.04 mmol, 1 eq) in MeOH (260 µl), H$_2$O (120 µl), and H$_2$SO$_4$ (20 µl) was heated at 90° C. until conversion of the dimethoxyacetal to aldehyde was complete as detected by ESI-MS analysis (24 h). The mixture was then allowed to cool to ambient temperature, diluted with H$_2$O (2 mL) and extracted with EtOAc (3×5 mL). The aqueous layer was then cooled in an ice-H$_2$O bath and the pH was increased to 12 with 5M NaOH. The aqueous layer was re-extracted with EtOAc (3×5 mL), dried over Na$_2$SO$_4$, filtered, and concentrated in vacuo. A portion of the crude aldehyde was used in the methotrexate hydrazide/isoxazolidine coupling reaction and the product was isolated by reverse-phase HPLC purification to provide 5 as yellow solid that was stored at −78° C., shielded from light. The purity of 5 was confirmed by analytical reverse-phase HPLC immediately after isolation and again prior to use in any in vitro transcription reactions. The identity was verified by mass spectral analysis of the isolated construct. UV ($\lambda_{max}$ nm): 257, 299, 376: HRMS (ESI) calcd for (C$_{38}$H$_{49}$N$_{11}$O$_7$+H)$_+$: 772.3895, found: 772.3886.

2-(2-Benzyl-5-dimethoxymethyl-3-isobutyl-isoxazolidin-3-yl)-ethanol (S8)

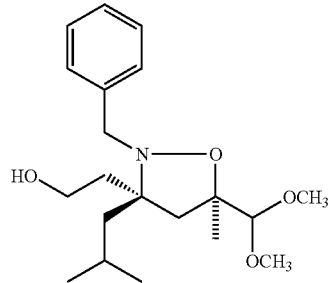

To a solution of diol S7 (15 mg, 0.04 mmol, 1 eq) in CH$_3$CN (20 µl) and H$_2$O (200 µl) cooled in an ice-H$_2$O bath was added NaIO$_4$ (0.01 g, 0.05 mmol, 1.2 eq). The reaction was allowed to warm to ambient temperature and stirred until complete by TLC analysis, typically within 1 h. The reaction was then diluted with H$_2$O (7 mL) and extracted with Et$_2$O (3×5 mL). The combined organic extracts were washed with H$_2$O (1×10 mL), and brine (1×10 mL), dried over Na$_2$SO$_4$, filtered, and concentrated in vacuo. The crude aldehyde (10 mg, 0.03 mmol, 1 eq) was dissolved in MeOH (0.31 mL) and cooled in an ice-H$_2$O bath to which NaBH$_4$ (3 mg, 0.08 mmol, 2.5 eq) was added. The reaction mixture was allowed to stir with continued cooling until complete by TLC analysis (30 min). The reaction was then quenched with H$_2$O (5 mL) and extracted with EtOAc (3×25 mL). The combined organic extracts were dried over Na$_2$SO$_4$, filtered, and concentrated in vacuo. Purification by flash chromatography (3:7 hexanes/EtOAc) provided 9.4 mg of dimethoxyacetal S8 in 70% yield as an oil. IR: 2915, 1456, 1069 cm$^{-1}$; $^1$H NMR (400 MHz): δ 0.98 (d, 3H, J=6.6), 0.99 (d, 3H, J=6.6), 1.44 (dd, 1H, J=1.3, 7.0), 1.50-1.60 (br s, 1H), 1.70-1.79 (m,3H), 1.91-2.00 (m, 1H), 2.21 (dd, 1H, J=12.8, 8.4), 2.28 (dd, 1H, J=12.8, 8.1), 3.30 (s, 3H), 3.40 (s, 3H), 3.79-3.85 (m, 3H), 3.98 (d, 1H, J=13.9), 4.15-4.20 (m, 1H), 4.32 (d, 1H, J=5.5), 7.19-7.32 (m, 5H); $^{13}$C NMR: d 23.75, 24.85, 25.12, 30.22, 35.27, 38.84, 42.45, 54.91, 55.19, 59.73, 70.51, 78.95, 105.46, 126.98, 128.28, 128.57, 138.09; HRMS(ESI) calcd for (C$_{19}$H$_{31}$NO$_4$+H)$_+$: 338.2327, found: 338.2331.

2-(4-({(6-(Amino-methylcarbaminidoylimino-methyl)-pyrazin-2-ylmethyl)-methylamino}-methyl)-benzoylamino)-4-(2-benzyl-(3RS)-(2-hydroxyethyl)-3-isobutylisoxazolidin-(5RS)-ylmethylenehydrazinocarbonyl)-(S)-butyric acid (4)

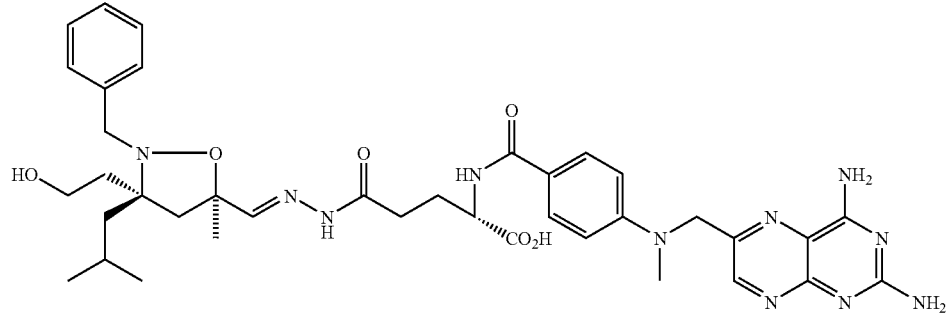

Deprotection of the dimethoxyacetal of S8 under the acidic conditions described for 5 liberated the aldehyde. A portion of the crude aldehyde was used immediately in the conjugation reaction with 1. Reverse-phase HPLC purification provided 4 as yellow solid (86% yield) that was stored at −78° C., shielded from light. The purity of 4 was confirmed by analytical reverse-phase HPLC immediately after isolation and again prior to use in any in vitro transcription reactions. The identity was verified by mass spectral analysis of the isolated construct. UV ($\lambda_{max}$ nm): 258, 300, 376; HRMS (ESI) calcd for $(C_{37}H_{47}N_{11}O_6+Na)_+$: 764.3608, found: 764.3633.

3-(2-Benzyl-5-(tert-butyl-dimethyl-silanyloxymethyl)-3-isobutyl-isoxazolidin-3-yl)-propane-1,2-diol (S9)

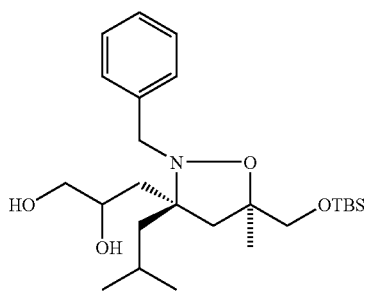

Dihydroxylation conditions were analogous to those used for the preparation of S7. Purification by flash chromatography (2:3 hexanes/EtOAc; $R_f$: 0.35 and 0.43) provided 65 mg of S9 in 81% yield and $_1$H NMR spectral integration revealed a 1:1 mixture of diastereomers at the newly formed 2° OH. IR: 3339, 2952, 1461, 1119, 835 cm$^{-1}$; $^1$H NMR (unresolved diastereomeric mixture at the 2° OH): δ 0.02-0.09 (6H), 0.87-0.91 (9H), 0.98-1.03 (6H), 1.60-2.38 (7H), 3.40-4.36 (10H), 7.25-7.38 (5H); HRMS (ESI) calcd for $(C_{24}H_{43}NO_4Si+Na)_+$: 460.2859, found: 460.2856.

3-(2-Benzyl-5-hydroxymethyl-3-isobutyl-isoxazolidin-3-yl)-propane-1,2-diol (S12)

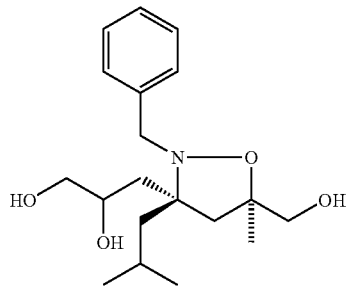

To a solution of S9 (37 mg, 0.09 mmol, 1 eq) in THF (850 µL) cooled in an ice-H$_2$O bath was added TBAF (85 µL of a 1M solution in THF, 0.18 mmol, 2 eq). The reaction mixture was allowed to stir with continued cooling until complete by TLC analysis (6 h). The reaction was then diluted with H$_2$O (50 mL) and extracted with EtOAc (3×15 mL). The combined organic extracts were dried over Na$_2$SO$_4$, filtered, and concentrated in vacuo. Purification by flash chromatography (95:5 CH$_2$Cl$_2$/MeOH; $R_f$: 0.17) provided 26 mg of S12 in 98% yield as an oil and $^1$H NMR spectral integration revealed a 1:1 mixture of diastereomers at the 2° OH. IR: 3348, 2952, 1453, 1042 cm$^{-1}$; $^1$H NMR (unresolved diastereomeric mixture at the 2° OH): δ 0.92-1.02 (6H), 1.34-1.78 (4H), 1.94-2.41 (4H), 3.40-3.85 (5H), 3.96-4.36 (3H), 7.24-7.35 (5H); HRMS (ESI) calcd for $(C_{18}H_{29}NO_4+H)_+$: 324.2175, found: 324.2167.

2-(4({(6-(Amino-methylcarbaminidoylimino-methyl)-pyrazin-2-ylmethyl)-methylamino}-methyl)-benzoylamino)-4-(2-(2-benzyl-(5RS)-hydroxymethyl-(3RS)-isobutylisoxazolidin-3-yl)-ethylidene-hydrazinocarbonyl)-(S)-butyric acid (6):

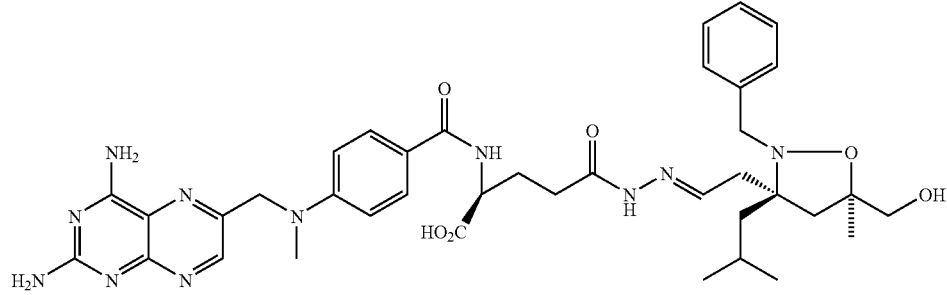

Oxidative cleavage of diol S12 was accomplished under the conditions described for S8, and a portion of the crude aldehyde was used immediately in the conjugation reaction with 1. Reverse-phase HPLC purification provided 6 as yellow solid (97% yield) that was stored at −78° C., shielded from light. The purity of 6 was confirmed by analytical reverse-phase HPLC immediately after isolation and again prior to use in any in vitro transcription reactions. The identity was verified by mass spectral analysis of the isolated construct. UV ($\lambda_{max}$ nm): 260, 299, 375; HRMS (ESI) calcd for $(C_{37}H_{47}N_{11}O_6+Na)_+$: 764.3608, found: 764.3616.

(5-(tert-Butyl-dimethyl-silanyloxymethyl)-3-(2,3-dihydroxy-propyl)-3-isobutylisoxazolidin-2-yl)acetic acid tert-butyl ester (S10)

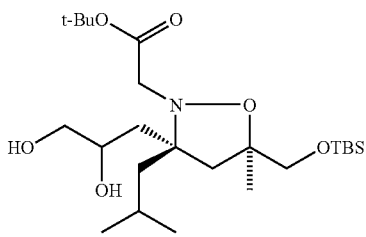

Dihydroxylation of S2 was accomplished under conditions identical to those used for S7. Purification of the crude reaction mixture by flash chromatography (2:8 hexanes/EtOAc; $R_f$: 0.30 and 0.35) provided 48 mg of S10 in 48% overall yield and $^1$H NMR spectral integration revealed a 2:1 mixture of diastereomers at the newly formed 2° OH. IR: 3369, 2953, 1733, 1155 cm$^{-1}$; $^1$H NMR (unresolved diastereomeric mixture at the 2° OH): δ 0.02-0.08 (6H), 0.86-0.98 (15H), 1.21-1.26 (2H), 1.42-1.52 (11H), 1.59-1.74 (2H), 2.06-2.22 (3H), 3.36-3.74 (6H), 3.84-4.34 (2H); ESI-MS calcd for $(C_{23}H_{47}NO_6Si+H)_+$: 462.3, found: 462.3.

(3-(2,3-dihydroxy-propyl)-5-hydroxymethyl-3-isobutyl-isoxazolidin-2-yl)acetic acid tert-butyl ester (S11)

To a solution of S10 (24 mg, 0.05 mmol, 1 eq) in EtOH (530 µL) cooled in an ice-H$_2$O bath was added 1N HCl until the pH was adjusted to 2 (about 3 drops). The reaction mixture was allowed to stir with continued cooling until complete by TLC analysis. The reaction was then diluted with H$_2$O (1 mL) and extracted with EtOAc (6×5 mL). The combined organic extracts were dried over Na$_2$SO$_4$, filtered, and concentrated in vacuo. Purification by flash chromatography (9:1 CH$_2$Cl$_2$/MeOH; $R_f$: 0.30) provided 18 mg of S11 in 95% yield as an oil and $^1$H NMR spectral integration revealed a 2:1 mixture of diastereomers at the 2° OH. IR: 3367, 2925, 1733, 1155 cm$^{-1}$; $^1$H NMR (unresolved diastereomeric mixture at 2° OH): d 0.88-0.97 (6H), 1.04-1.31 (2H), 1.44-1.53 (9H), 1.62-1.71 (2H), 1.88-2.10 (1H), 2.16-2.24 (2H), 3.28-3.61 (5H), 3.82-3.86 (1H), 3.94-4.35 (2H); ESI-MS calcd for $(C_{17}H_{33}NO_6+H)_+$: 348.2, found: 348.2.

2-(4({(6-(Amino-methylcarbaminidoylimino-methyl)-pyrazin-2-ylmethyl)-methylamino}-methyl)-benzoylamino)-4-{2-((5RS)-hydroxymethyl-2-(hydroxy-2-oxopropyl)-(3RS)-isobutyl-isoxazolidin-3-yl)-ethylidene-hydrazinocarbonyl}-(S)-butyric acid (3)

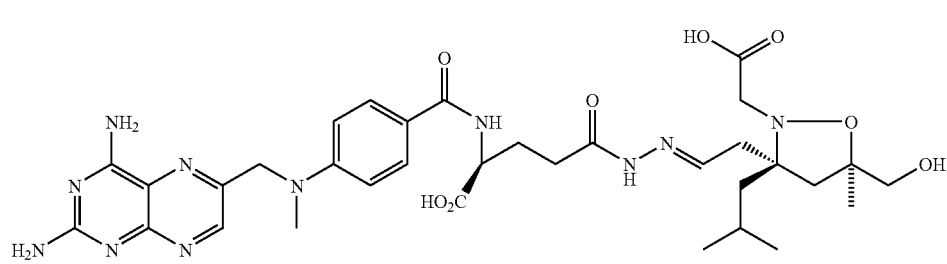

3

To S11 (8.8 mg, 0.03 mmol, 1 eq) was added 500 mL of a freshly made solution of TFA/triisopropylsilane/H$_2$O (95:2.5:2.5) cooled in an ice-H$_2$O bath. Once complete by TLC, the reaction was concentrated under high vacuum and the mixture was subjected to the diol oxidative cleavage conditions described for S8. The crude aldehyde thus obtained was used immediately in the conjugation reaction with 1. Reverse-phase HPLC purification provided 3 as yellow solid that was stored at −78° C., shielded from light. The purity of 3 was confirmed by analytical reverse-phase HPLC immediately after isolation and again prior to use in any in vitro transcription reactions. The identity was verified by mass spectral analysis of the isolated construct UV ($\lambda_{max}$ nm): 260, 300, 372: ESI-MS calcd for $(C_{32}H_{43}N_{11}O_8+H)_+$: 710.3, found: 710.2.

Acetic acid (2-benzyl-3-(2-hydroxy-ethyl)-3-isobutyl-isoxazolidin-5-ylmethylene)-hydrazide (S13)

S13

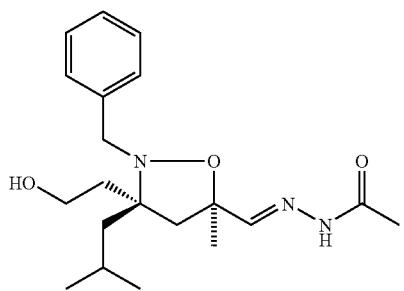

Deprotection of the dimethoxyacetal of S8 under the acidic conditions described for 5 liberated the aldehyde. A portion of the crude aldehyde (3 mg, 0.01 mmol, 1 eq) in THF (480 μL) was added to acetic hydrazide (0.7 mg, 0.01 mmol, 1 eq) in THF (480 μL). The reaction was stirred at ambient temperature for 12 h. The mixture was then concentrated to dryness under high vacuum (0.05 mm Hg) and subjected to normal phase HPLC purification to provide 2.5 mg of S13 as colorless oil. $R_f$: 0.21 (1:4 hexanes/EtOAc). IR: 3200, 2954, 2923, 1674, 1370 cm$^{-1}$; $^1$H NMR (400 MHz): δ 1.00 (d, 3H, J=6.6), 1.03 (d, 3H, J=6.6), 1.16-1.20 (m, 1H), 1.74-2.08 (m, 4H), 2.22 (s, 3H), 2.40-2.45 (m, 1H), 2.55 (dd, 1H, J=12.5, 8.1), 3.75 (d, 1H, J=11.4), 3.85-3.98 (m, 2H), 4.13 (d, 1H, J=11.0), 4.75 (d, 1H, J=5.9), 7.10 (d, 1H, J=5.5), 7.22-7.38 (m, 5H), 8.73 (br s, 1H); HRMS (ESI) calcd for $(C_{19}H_{29}N_3O_3+H)_+$: 348.2287, found: 348.2283.

EXAMPLE 3

Isozazolidine Based Activation Domains

To identify a minimal functional unit for a small molecule-based activation domain, a series of isoxazolidines containing functional groups typically found in endogenous activation domains were designed (See, e.g., FIG. 5a). This heterocyclic scaffold was chosen due to the relative ease with which diverse functional groups could be incorporated in a stereo controlled manner onto the conformationally constrained ring, (See, e.g., Kanemasa et al., J. Am. Chem. Soc. 116, 2324 (1994); Bode et al., Angew. Chem., Int. Ed., 40, 2082 (2001); Minter et al., J. Am. Chem. Soc. 125, 6846 (2003)) thus displaying those groups in a three-dimensional array. Key functional groups found in ATF14 and related activation domains include phenyl, hydroxyl, carboxylic acid, and isobutyl groups. Isoxazolidine 2 has three hydrophobic groups appended at the N2 and C3 positions, while isoxazolidines 3-6 each have a combination of polar (hydroxyl and carboxylic acid) and hydrophobic groups (phenyl, isobutyl) at N2, C3, and C5 (See, e.g., FIG. 5a). The relative stereochemistry at C3 and C5 in key intermediate 7 was set via addition of an allyl Grignard to isoxazoline 8 (See, e.g., Minter et al., J. Am. Chem. Soc. 125, 6846 (2003)) and alkylation of N2 served to introduce the benzyl or acid group at that position. The final step of the syntheses of 2-6 was hydrazone formation with methotrexate hydrazide (1), used to localize the isoxazolidines to DNA in functional assays. ATF14 was also synthesized and coupled to methotrexate to enable a direct functional comparison with the small molecules.

An in vitro transcription assay was employed to assess the capability of each of the isoxazolidines to function as transcriptional activation domains under standard conditions (See, e.g., FIG. 5C; Lue et al., Methods Enzymol. 194, 545 (1991); Lee and Roeder, Mol. Cell. Biol. 1, 635 (1981); Liu et al., Biochem. 300, 40 (2002)). For example, in this assay, the fusion protein LexA-DHFR11 serves as the DNA binding domain, localizing the isoxazolidines to the promoter via the specific and high affinity methotrexate-DHFR binding interaction. This is a robust interaction tolerant of a range of substitution at the γ-carboxy position of methotrexate (See, e.g., Miller et al., Angew. Chem., Int. Ed. 43, 1672 (2004); Braun et al., J. Am. Chem. Soc. 125, 7575 (2003); Benkovic et al., Science 239, 1105 (1988)). For each experiment, compound 1 (negative control), isoxazolidines 2-6, or ATF14 (coupled to methotrexate) were combined with a DNA template consisting of a reporter gene under the control of two LexA binding sites within an AdML promoter, followed by addition of HeLa nuclear extracts and nucleotide triphosphates. mRNA production was directly measured and used to determine the activity of all compounds, displayed as percent activation relative to the positive control ATF14 (FIG. 5c).

Isoxazolidine 4 is nearly as active as the positive control ATF14 despite a considerable difference in size (MW 290 versus 1674). It is also the most potent of all of the isoxazolidines examined, with ~5- to ~7-fold levels of activation over basal. This function is dependent upon a DNA binding domain, as an identically functionalized isoxazolidine lacking covalently linked methotrexate does not activate transcription and also competitively inhibits transcription mediated by 4 (See, e.g., Example 5). Similar to natural activation domains such as ATF14, a balance of hydrophobicity and polarity appears to participate in overall potency (See, e.g., Drysdale et al., Mol. Cell. Biol. 15, 1220 (1995); Regier et al., Proc. Natl. Acad. Sci. U.S.A. 90, 883 (1993); Lin et al., J. Genes Dev. 8, 1235 (1994); Sullivan et al., Nucleic Acids Res. 26, 4487 (1998)). Substantially increasing the hydrophobicity (See, e.g., FIG. 5C, conjugate 2) or the polarity (See, e.g., FIG. 5C, conjugate 3) leads to a dramatic decrease in function. In contrast, slightly increasing the polarity at C3 by incorporation of an additional hydroxyl (See, e.g., FIG. 5C, conjugate 5) is well tolerated. Consistent with a preferred orientation of the hydrophobic and polar substituents, isoxazolidine 6, containing the same functional groups as 4, shows reduced activation potential (See, e.g., FIG. 5C, conjugate 6).

EXAMPLE 4

Further Characterization of 4 (2-(4({(6-(Amino-methylcarbaminidoylimino-methyl)-pyrazin-2-ylmethyl)-methylamino}-methyl)-benzoylamino)-4-(2-benzyl-(3RS)-(2-hydroxy-ethyl)-3-isobutylisoxazolidin-(5RS)-ylmethylene-hydrazinocarbonyl)-(S)-butyric acid)

Figure 1:
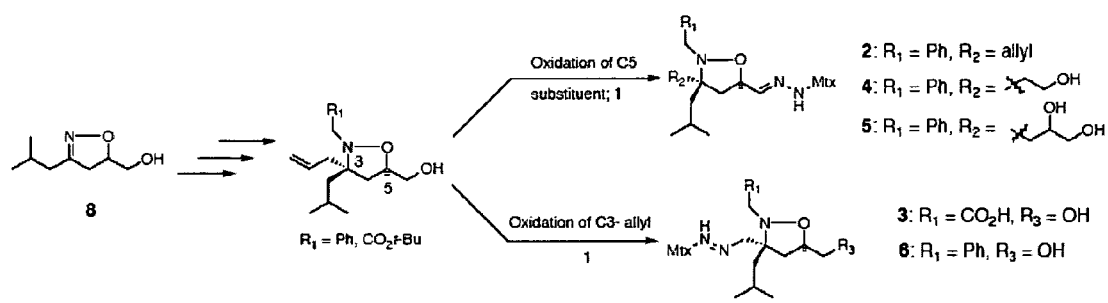
FIG. 1 depicts general strategies for synthesis of conjugates.
Figure 2:
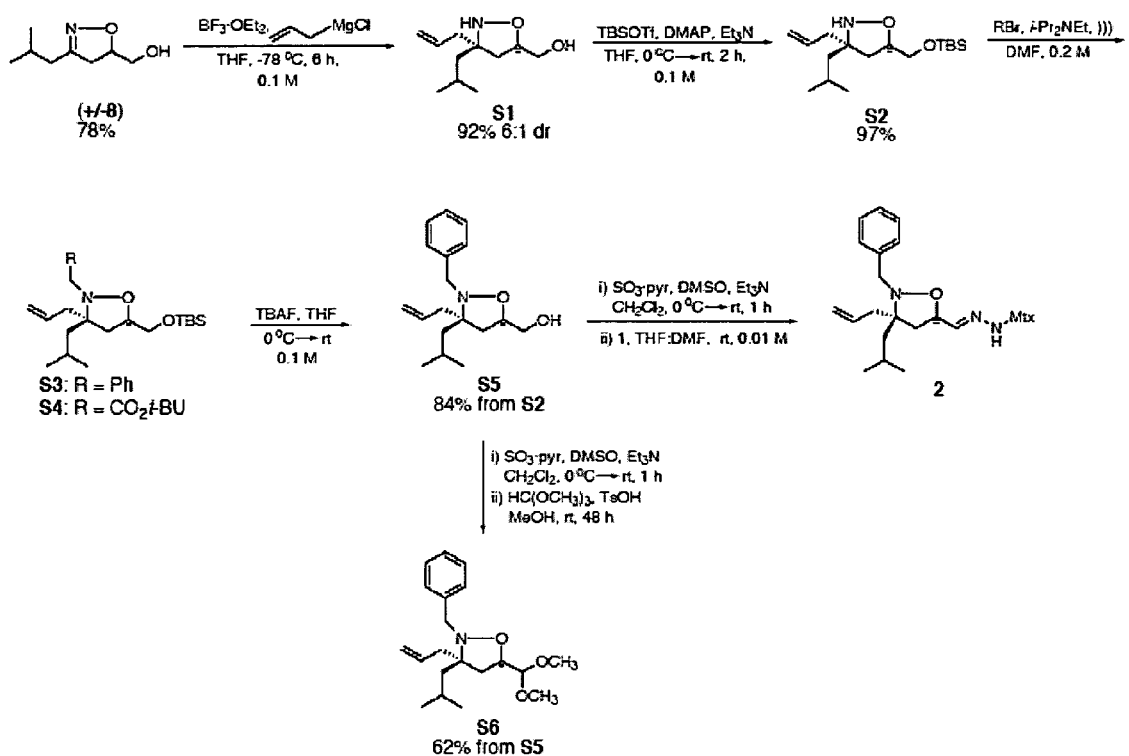
FIG. 2 depicts a scheme for synthesizing activation domains.
Figure 3:
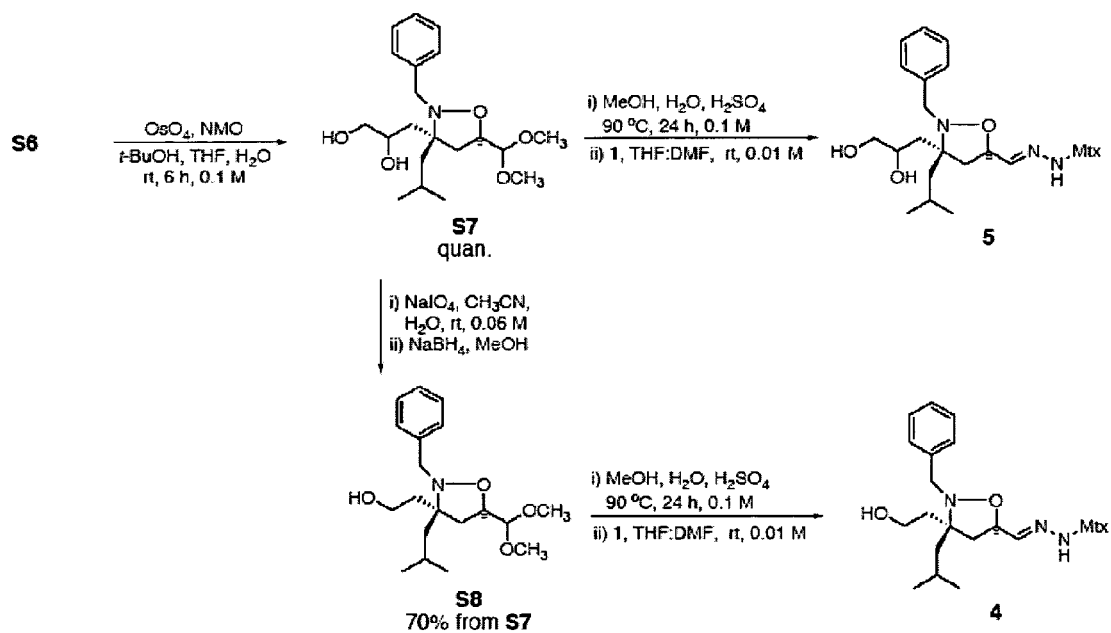
FIG. 3 depicts a second scheme for synthesizing activation domains.
Figure 4:
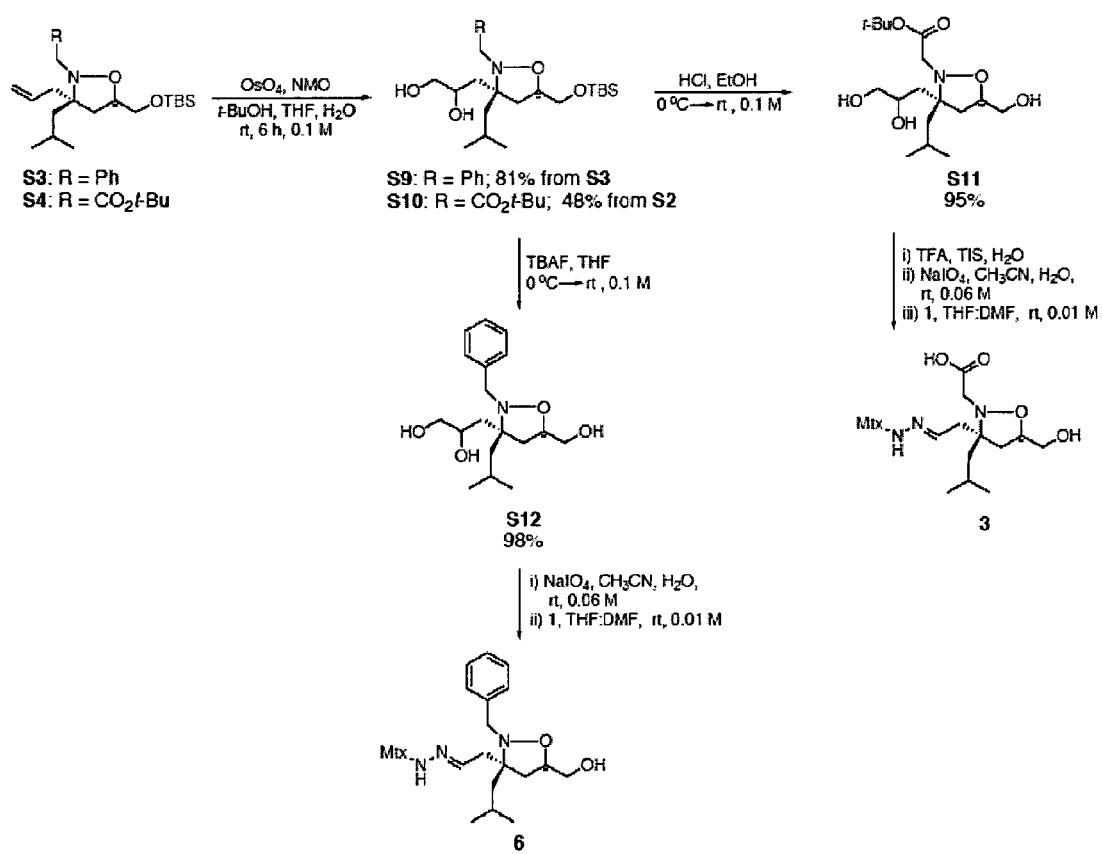
FIG. 4 depicts a third scheme for synthesizing activation domains.
Figure 6:
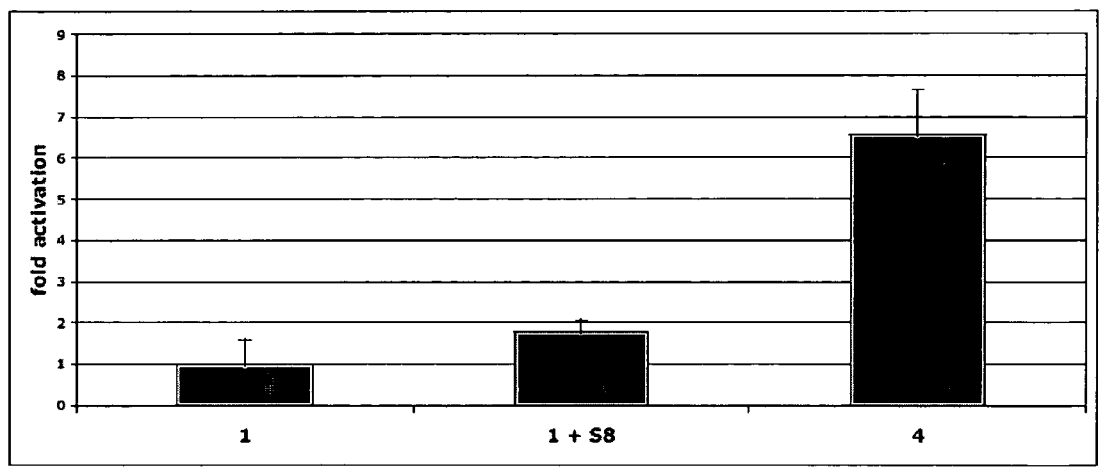
FIG. 6 depicts levels of activation by an activation domain in presence and absence of covalent bonding to methotrexate.

In order to show activation is dependant on the covalent bond between methotrexate and the isoxazolidine, an experiment was carried out in which the two components were added separately in the same reaction. Since 4 showed the strongest levels of activation, it was chosen for further studies. In this experiment the levels of transcriptional activation obtained with 1 alone (negative control) and 4 were compared with reactions containing S8 and 1 to probe the dependence of function on DNA binding. Little activation was observed when the small molecule activation domain was not localized to DNA (See, e.g., FIG. 6).

EXAMPLE 5

Competition/squelching Experiments

Figure 7:
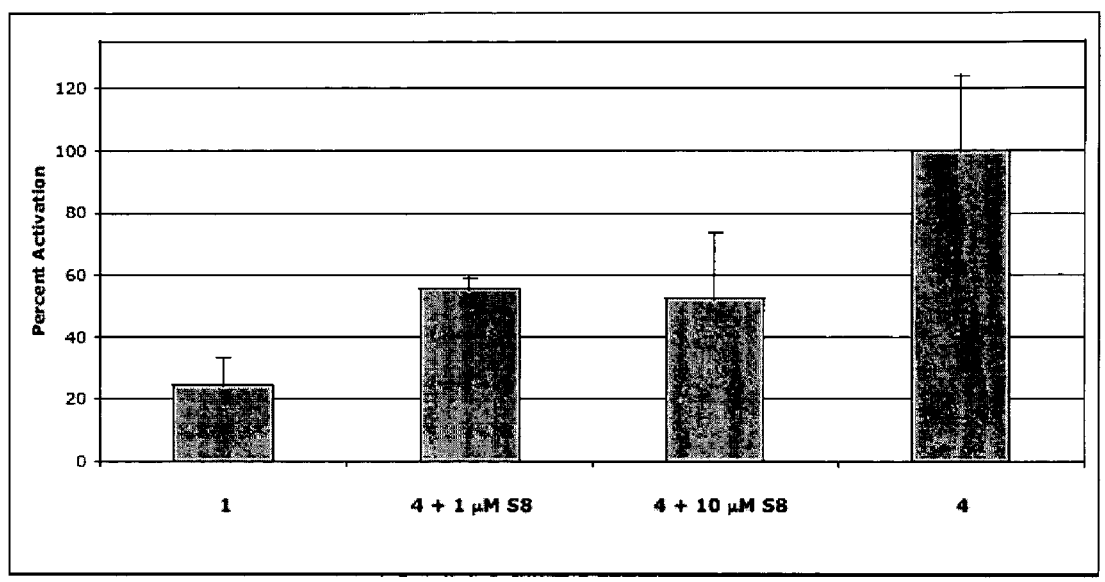
FIGS. 7 and 8 depict competition/squelching experiments conducted with activation domains of the present invention.
Figure 8:
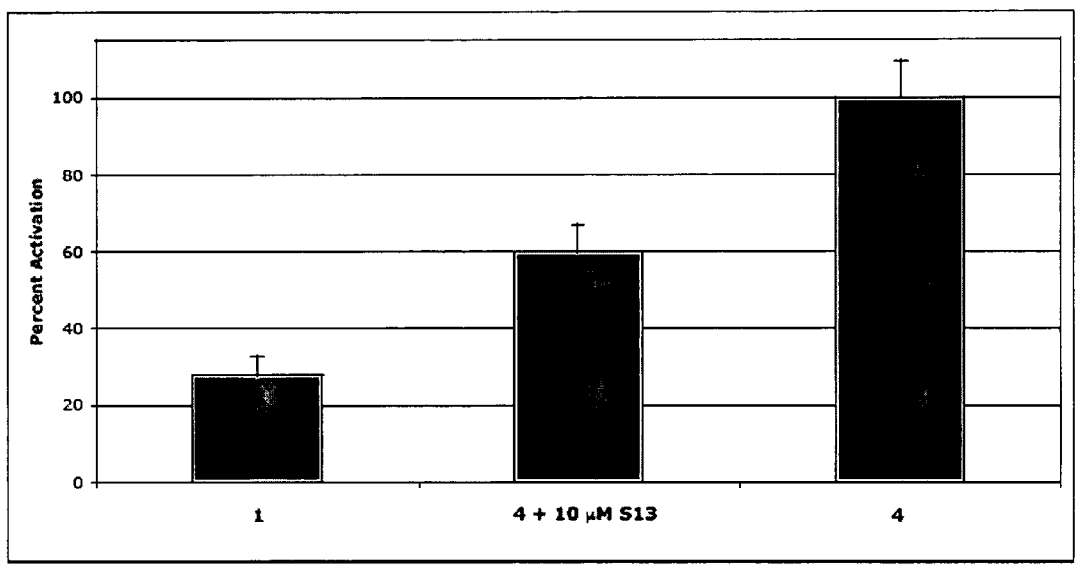

As a further demonstration that 4 activates transcription by binding to DNA and then recruiting the transcriptional machinery, a "squelching" experiment was carried out (See, e.g., Gill and Ptashne, Nature 334, 721 (1988); Tasset et al., Cell 62, 1177 (1990)). In this experiment, micromolar concentrations of free activation domain are added to transcription reactions containing the DNA-bound activator and the corresponding affect on transcription levels is measured. Results with one of the activation domains (4) is shown (See, e.g., FIGS. 7-8). As depicted in FIG. 7, a 1-10 μM concentration of acetal S8 was sufficient to suppress transcription mediated by 4 nearly 50%, consistent with previous squelching experiments, indicating that the free activation domain and the DNA-bound activator target the same proteins (See, e.g., Gill and Ptashne, Nature 334, 721 (1988); Tasset et al., Cell 62, 1177 (1990); Mapp et al., Proc. Natl. Acad. Sci. U.S.A. 97, 3930 (2000)). To probe the effect of the hydrazone linkage on function, the same experiment was carried out with 4 and hydrazone with similar results (See, e.g., FIG. 8).

EXAMPLE 6

Rapid Screen for Small Molecule Protein Ligands

The activation domains of the present invention can be used to identify small molecule-protein interactions (e.g., for the discovery of ligands for specific proteins). Such an assay is an enormously powerful tool for rapidly identifying ligands for specific proteins in the context of the cell, with applications in pharmaceutical and basic research.

A protein of interest is fused to a DNA binding domain, analogous to the original two-hybrid assay (See, e.g., Example 6, FIG. 12). Attached to the small molecule transcriptional activation domain (See, e.g., FIGS. 1 and 5a) is a combinatorial library of compounds. If one of the members of the combinatorial library is a ligand for the protein of interest, a transcriptional activator is reconstituted and the reporter gene is turned on. This assay can be carried out in a variety of cell types (e.g., bacteria, yeast or mammalian cells) with a variety of reporter genes (e.g., β-galactosidase). Compounds that bind to the protein of interest, as determined by reporter gene expression, can then be identified.

EXAMPLE 7

Small Molecule Inducers of Gene Expression

The small molecule transcriptional activators of the present invention offer a powerful tool for the regulated and fine tuned expression of endogenous genes. When coupled to a DNA binding domain that targets a specific endogenous promoter, the small molecule activators can simply be added to the culture media to rapidly induce expression of a targeted gene or set of genes. The advantage of this type of system is that the levels of gene activation can be fine tuned by choosing one of several different small molecule transcriptional activation domains (e.g., use of a potent activation domain to activate high levels of gene expression or use of a weak activation domain to activate low levels of gene expression).

EXAMPLE 8

Transcription Based Therapeutics

The activation domains of the present invention can be used to regulate expression of a gene of interest in a subject. For example, a battery of human diseases are characterized by aberrant transcription patterns (e.g., acute promyelotic leukemia). The present invention provides a method of regulating expression of a gene of interest in a subject comprising the administration of an activation domain fused to a DNA binding domain such that the expression of an aberrantly expressed gene is modified (e.g., is activated or repressed). Furthermore, the present invention provides a method of treating a subject with symptoms of disease by providing the subject with a therapeutic formulation comprising an activation domain fused to a DNA binding domain under conditions such that the symptoms are reduced.

EXAMPLE 9

Isoxazolidine Small Molecule ADs Mimic the Functional Profile of Natural ADs

This example describes positional "mutagenesis" in which analogs of 1 of FIG. 13 (e.g., bearing identical side chains in various locations within the isoxazolidine scaffold) were evaluated for transcriptional activity.

In previous examples, each of the isoxazolidines were prepared as racemates and tested as stereoisomeric mixtures. Thus, in this series of experiments, each enantiomer of the isoxazolidine (See FIG. 14A, 3 and 4) as well as a diastereomer (See FIG. 14A, 5) and two positional isomers (See FIG. 14A, 6 and 7) were targeted. The compounds contain the same functional groups found in 1 of FIG. 13, but in varying three-dimensional orientations since significantly altering the hydrophobic and polar content of the molecules was found to decrease function (See Example 3, above).

The key intermediate for the preparation of 3, 5, and 6 is isoxazoline 10 (See FIG. 14B), isolated as a single enantiomer in 88% yield following a 1,3-dipolar cycloaddition reaction (See, e.g., Kanemasa et al., J. Am. Chem. Soc. 1994, 116, 2324-39; Bode et al., Chem., Int. Ed. 2001, 40, 2082-5). Toward 6 (See FIG. 14B), installation of the C3 benzyl group was accomplished by silyl protection of the secondary alcohol of 10 followed by addition of benzylmagnesium chloride (80% yield; 10:1 dr) (See, e.g., Minter et al., J. Am. Chem. Soc. 2003, 125, 6846-7). The major diastereomer was then treated with allyl bromide under microwave conditions to alkylate N2 and provide isoxazolidine 13 (65% yield). Oxidative cleavage of the double bond installed the requisite hydroxyl group on the N2 side chain, and treatment with TBAF unmasked the 1,2-diol that was cleaved to provide an aldehyde at C5; this sensitive intermediate was immediately combined with Mtx (See FIG. 14A) and the resulting conjugate 6 isolated by reversed-phase HPLC. For diastereomers 3 and 5 (See FIG. 14A), allylmagnesium chloride was employed as the nucleophile in the initial addition reaction. Unlike the benzyl addition, the secondary alcohol was not protected in order to reduce the diastereoselectivity of the reaction and enable both diastereomers (11 and 12) to be isolated (71% combined yield, 5:1 dr). The two diastereomers were separated chromatographically, and each underwent installation of the N2 benzyl group via alkylation (81% yield) and oxidative cleavage of the C3 allyl group to provide 14 and 15 (See FIG. 14B). Straightforward manipulations lead to the final conjugate targets 3 and 5 (See FIG. 14A). Isoxazolidine 4 was prepared through an analogous reaction sequence starting with the enantiomer of 9 (See FIG. 14B).

The function of the isoxazolidines was measured by their ability to up-regulate transcription in a standard in vitro transcription assay employing HeLa (human) nuclear extracts with the natural AD ATF14 as a positive control (See FIG. 15). The activity of enantiomers 3 and 4 is indistinguishable from that of AD 1 containing both enantiomers of the isoxazolidine ring (See FIG. 15). Although an understanding of the mechanism is not necessary to practice the present invention and the present invention is not limited to any particular mechanism of action, isoxazolidines 5-7 more significantly differ in the presentation of the amphipathic functional groups due to stereo chemical changes (5) or positional changes within the ring (6 and 7). Nonetheless, the small molecules function well as transcriptional ADs. Isoxazolidine 7 showed the only noteworthy attenuation in activity, with 35% lower functional levels relative to 1 (~4-fold). Thus, the present invention provides that precise positioning of functional groups is not the most important determinant of activator function.

The conserved activity across amphipathic, isomeric isoxazolidines 3-7 parallels the functional behavior of the endogenous amphipathic ADs. For example, the activity of 3 and 4 does not contradict an earlier report that the D and L-enantiomers of the natural AD ATF29 stimulate similar transcription levels in a cell-free system (See, e.g., Nyanguile et al., Proc. Natl. Acad. Sci. U.S.A. 1997, 94, 13402-6). Among peptidic ADs, a variety of combinations of polar and hydrophobic amino acids function as ADs, but a hydrophobic/polar balance is conserved (See, e.g., Ptashne and Gann, Genes & Signals; Cold Spring Harbor Laboratory: New York, 2001; Ma and Ptashne, Cell 1987, 51, 113-9; Giniger and Ptashne, Nature 1987, 330, 670-2; Melcher, Mol. Biol. 2000, 301, 1097-112). Further, similar to the small molecule activation domains of the present invention, endogenous ADs share a common structural motif; for natural ADs, structural studies suggest that formation of a helix occurs upon binding to a number of transcriptional machinery targets, although other secondary structures may play a role (See, e.g., Kussie et al., Science 1996, 274, 948-53; Radhakrishnan et al., Cell 1997, 91, 741-52; Uesugi et al., Science 1997, 277, 1310-3; Parker, D.; Jhala et al., Mol. Cell 1998, 2, 353-9). Also similar to the isoxazolidines, mutations in natural ADs that disrupt the hydrophobic surface significantly decrease activation potential (See, e.g., Regier et al., Proc. Natl. Acad. Sci. U.S.A. 1993, 90, 883-7; Drysdale et al., Mol. Cell. Biol. 1995, 15, 1220-33; Uesugi and Verdine, Proc. Natl. Acad. Sci. U.S.A. 1999, 96, 14801-6).

Thus, the present invention demonstrates that isoxazolidines are unlikely to be the only suitable scaffolds for the construction of small molecule transcriptional activation domains. Rather, the present invention provides that a variety of appropriately functionalized conformationally constrained small molecules (e.g., comprising both hydrophobic as well as polar regions) function well as activation domains (e.g., form a helix upon binding to targets (e.g., transcriptional machinery targets or nucleic acit)). Thus, the present invention obviates the need to identify high affinity ligands for single protein targets and takes advantage of the remarkable functional flexibility characteristics of the endogenous transcriptional regulatory system.

EXAMPLE 10

Small Molecule Activation Domains can Inhibit Activity of Endogenous Transcriptional Activation Domains Isoxazolidine is able to competitively inhibit the activity of a classic peptidic transcriptional activation domain, AH, when added to S. cerevisiae cultures. Inhibition observed with increasing small molecule concentrations demonstrates that small molecule activation domains of the present invention target at least a subset of the coactivators of the peptidic molecule (See FIG. 16). For these experiments, cultures obtained from individual yeast colonies were treated with either DMSO ('untreated') or isoxazolidine dissolved in DMSO and inhibition of Gal4(1-100)+AH was assessed using a standard β-galactosidase assay. At a concentration of 10 mM, approximately 25% inhibition is observed (e.g., consistent with a model in which the isoxazolidine activation domain interacts with the same coactivators as does AH). Thus, the present invention demonstrates that the isoxazolidine family of activators provided in the present invention are effective as transcriptional inhibitors (e.g., of endogenous transcriptional activators).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition comprising a transcriptional activation domain, said activation domain comprising an isoxazolidine, wherein said isoxazolidine is:

a)

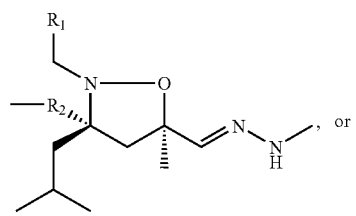

b)

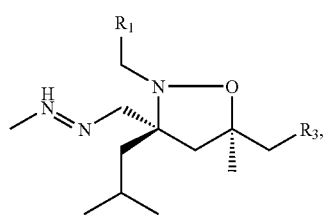

wherein R1 is a phenyl or CO₂H, wherein R2 is an allyl,

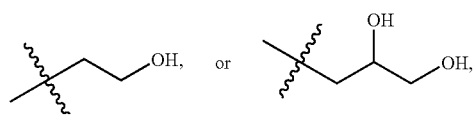

and wherein R3 is OH.

2. The composition of claim 1, wherein said activation domain is selected from the group consisting of:

a)

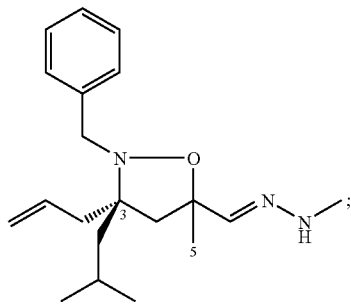

b)

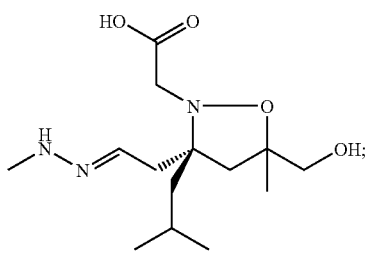

c)

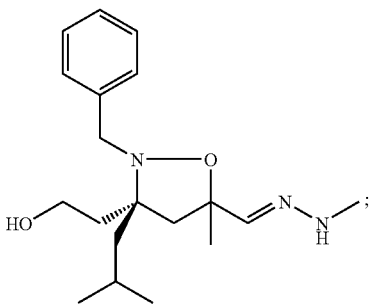

d) 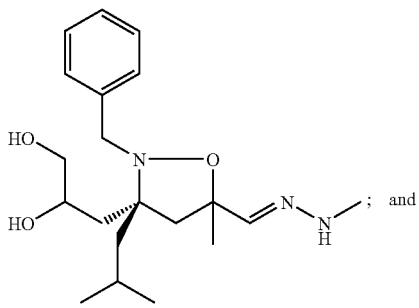

e) 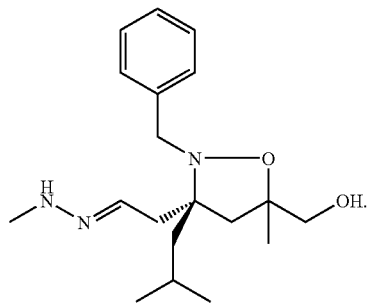

3. The composition of claim 1, wherein said isoxazolidine is oligomerized.

4. The composition of claim 1, wherein said activation domain is fused to a DNA binding domain.

5. The composition of claim 4, wherein said DNA binding domain is specific for a promoter region in a gene.

6. The composition of claim 5, wherein said gene is selected from the group consisting of: abl, Bcl-2, Bcl-xL, erb, fms, gsp, hst, jun, myc, neu, raf, ras, ret, src, trk, BRCA1, BRCA2, C-CAM, p16, p21, p53, p73, Rb, p27, KDR, Renin, C-raf, NOS, NOS(I), ERK7, MAPK, Fms-TK, PKC-α, PKC-α1, PKC-β, SAPK-α, CDK2, Chp-JNK, Ha-ras, C-fos, bc1-2, NF-κB, Cyclin-E AP-1, c-Fos, c-Jun, NF-E2, CRE-BP1, ATF, CREB, C/EBP, NF-IL6, MyoD, E2F, USF, NF-1, RF-X, CP1, ER, GR, PR, RAR, RXR, T3R, COUP, GATA-1, Sp1, YY1, GAL4, EN, HNF-1, OCT, HNF-3, c-Myb, Ets, IRF-1, G3PDH, N/K ATPase, Ca-ATPase, IL-1β, IL-5, IL-6, IL-4, IFN-γ, MIP-1α, MIP-2, MCP-1, RANTES, TNF-α, TNF-αR1, TGF- β, and TGF-βR1.

7. The composition of claim 1, wherein said activation domain is coupled to a compound, wherein said compound is one of a plurality of compounds of a compound library.

8. The composition of claim 7, wherein said compound library comprises putative ligands selected from the group consisting of carbohydrates, monosaccharides, oligosaccharides, polysaccharides, amino acids, peptides, oligopeptides, polypeptides, proteins, nucleosides, nucleotides, oligonucleotides, polynucleotides, lipids, retinoids, steroids, glycopeptides, glycoproteins, proteoglycans, and synthetic small molecule organic compounds.

* * * * *

SEQUENCE LISTING

```
<160> NUMBER OF SEQ ID NOS: 6

<210> SEQ ID NO 1
<211> LENGTH: 99
<212> TYPE: DNA
<213> ORGANISM: Artificial Sequence
<220> FEATURE:
<223> OTHER INFORMATION: Synthetic

<400> SEQUENCE: 1
agctttgagg acgaacgcgc ccccacccccc ttttatagcc cccccttcagg aacacctgag    60 ccgattgctg gcgatcaacg cgtaaagccg atagccgac                            99

<210> SEQ ID NO 2
<211> LENGTH: 99
<212> TYPE: DNA
<213> ORGANISM: Artificial Sequence
<220> FEATURE:
<223> OTHER INFORMATION: Synthetic

<400> SEQUENCE: 2
ctaggtcggc tatcggcttt acgcgttgat cgccagcaat cggctcaggt gttcctgaag    60
gggggctata aaagggggtg ggggcgcgtt cgtcctcaa                            99

<210> SEQ ID NO 3
<211> LENGTH: 88
<212> TYPE: DNA
<213> ORGANISM: Artificial Sequence
<220> FEATURE:
<223> OTHER INFORMATION: Synthetic

<400> SEQUENCE: 3
gatccactgc tgtatataaa accagtggtt atatgtacag tagactgctg tatataaaac    60
cagtggttat atgtacagta gagatctt                                        88

<210> SEQ ID NO 4
<211> LENGTH: 88
<212> TYPE: DNA
<213> ORGANISM: Artificial Sequence
<220> FEATURE:
<223> OTHER INFORMATION: Synthetic

<400> SEQUENCE: 4
aattaagatt cctactgtac atataaccac tggttttata tacagcagtc tactgtacat    60
ataaccactg tttttatata cagcagtg                                        88

<210> SEQ ID NO 5
<211> LENGTH: 30
```

```
<212> TYPE: DNA
<213> ORGANISM: Artificial Sequence
<220> FEATURE:
<223> OTHER INFORMATION: Synthetic

<400> SEQUENCE: 5
tatgaaaaaa agttaagacc tatgctcgct                                        30

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
gcgcagcgag cataggtctt aactttttt ca                                      32
```